United States Patent [19]
D'Antonio et al.

[11] Patent Number: 6,056,716
[45] Date of Patent: May 2, 2000

[54] HYPODERMIC FLUID DISPENSER

[75] Inventors: Nicholas F. D'Antonio, Liverpool; Linda F. D'Antonio, Syracuse, both of N.Y.; John T. Wagner, Drexel Hill, Pa.

[73] Assignee: D'Antonio Consultants International Inc., N.Y.

[21] Appl. No.: 08/738,303

[22] Filed: Oct. 25, 1996

Related U.S. Application Data

[63] Continuation-in-part of application No. 08/253,416, Jun. 3, 1994, Pat. No. 5,569,190, which is a continuation-in-part of application No. 07/818,235, Jan. 8, 1992, Pat. No. 5,318,522, which is a continuation-in-part of application No. 07/336,636, Apr. 7, 1989, Pat. No. 5,080,648, which is a continuation of application No. 07/059,620, Jun. 8, 1987, abandoned.

[51] Int. Cl.[7] ................................................. A61M 5/30
[52] U.S. Cl. ............................................. 604/68; 604/134
[58] Field of Search ............................... 604/68, 72, 198, 604/207, 46, 47, 131, 134

[56] References Cited

U.S. PATENT DOCUMENTS

| | | |
|---|---|---|
| 1,880,354 | 10/1932 | Mueller . |
| 2,675,802 | 4/1954 | Hein . |
| 2,762,369 | 9/1956 | Venditty . |
| 2,800,903 | 7/1957 | Smoot . |
| 3,134,380 | 5/1964 | Armao . |
| 3,136,313 | 6/1964 | Enstrom et al. . |
| 3,138,157 | 6/1964 | Ziherl et al. . |
| 3,262,449 | 7/1966 | Pannier et al. . |
| 3,419,007 | 12/1968 | Love . |
| 3,430,626 | 3/1969 | Bergman . |
| 3,490,451 | 1/1970 | Yahner . |
| 3,526,225 | 9/1970 | Isobe . |
| 3,557,784 | 1/1971 | Shields . |
| 3,649,299 | 3/1972 | Sholl . |
| 3,888,239 | 6/1975 | Rubinstein . |
| 3,945,383 | 3/1976 | Bennett et al. . |
| 3,948,266 | 4/1976 | Clark et al. . |
| 3,985,535 | 10/1976 | Bennett et al. . |
| 4,010,747 | 3/1977 | Clark et al. . |
| 4,014,206 | 3/1977 | Taylor . |
| 4,059,107 | 11/1977 | Iriguchi et al. . |
| 4,103,684 | 8/1978 | Ismach . |
| 4,165,800 | 8/1979 | Doherty et al. . |
| 4,196,730 | 4/1980 | Wilson . |
| 4,266,541 | 5/1981 | Landau . |
| 4,392,859 | 7/1983 | Dent ..................................... 604/198 |
| 4,396,384 | 8/1983 | Dettbarn et al. . |
| 4,410,323 | 10/1983 | Hodosh et al. . |
| 4,413,991 | 11/1983 | Schmitz et al. . |

(List continued on next page.)

FOREIGN PATENT DOCUMENTS

| | | | |
|---|---|---|---|
| 0087314 | 8/1959 | Denmark . | |
| 1424853 | 9/1988 | U.S.S.R. ............................... 604/68 |
| WO 91/12839 | 9/1991 | WIPO ................................... 604/68 |

OTHER PUBLICATIONS

"Mode of Operation of the Compressor in a Jet Injector," *Meditsinskava Techniko*, vol. 11, No. 1, pp. 23–27, Jan.–Feb., 1977.

"Comparative Evaluation of Three Jet Injectors for Mass Immunization," *Canadian Journal of Public Health*, vol. 68, pp. 513–516, Nov.–Dec., 1977.

"Efficacy of an Absorbed Trivalent Split Influenza Vaccine Administered by Intradermal Route," *Arch. Roum. Path., Exp. Microbiol.*, T 40, No. 1, pp. 67–70, Jan.–Mar., 1981.

*Primary Examiner*—Ralph A. Lewis
*Attorney, Agent, or Firm*—D. Peter Hochberg; William H. Holt

[57] ABSTRACT

A jet injector system for injecting fluid into a body. The jet injection system includes capsules for holding the material to be injected, apparatus for applying force to the capsule(s) to eject the injection material(s) and a perforator for directing the jet stream for the respective materials into the body. A flyweight system is described for developing jet injection pressures, and latching devices control the flyweight system. An injector system for injecting more than one fluid is described.

18 Claims, 23 Drawing Sheets

U.S. PATENT DOCUMENTS

| | | |
|---|---|---|
| 4,416,663 | 11/1983 | Hall . |
| 4,424,057 | 1/1984 | House . |
| 4,518,385 | 5/1985 | Lindmayer et al. . |
| 4,529,401 | 7/1985 | Leslie et al. . |
| 4,552,277 | 11/1985 | Richardson et al. . |
| 4,592,742 | 6/1986 | Landau . |
| 4,623,332 | 11/1986 | Lindmayer et al. . |
| 4,642,099 | 2/1987 | Phillips et al. .......................... 604/198 |
| 4,668,220 | 5/1987 | Hawrylenko . |
| 4,680,027 | 7/1987 | Parsons et al. ............................ 604/68 |
| 4,687,465 | 8/1987 | Prindle et al. . |
| 4,753,638 | 6/1988 | Peters . |
| 4,784,640 | 11/1988 | Johnson et al. . |
| 5,026,343 | 6/1991 | Holzer . |
| 5,080,648 | 1/1992 | D'Antonio ............................... 604/72 |
| 5,304,128 | 4/1994 | Haber et al. ............................ 604/68 |
| 5,318,522 | 6/1994 | D'Antonio . |
| 5,480,381 | 1/1996 | Weston ..................................... 604/68 |
| 5,569,190 | 10/1996 | D'Antonio ............................... 604/72 |

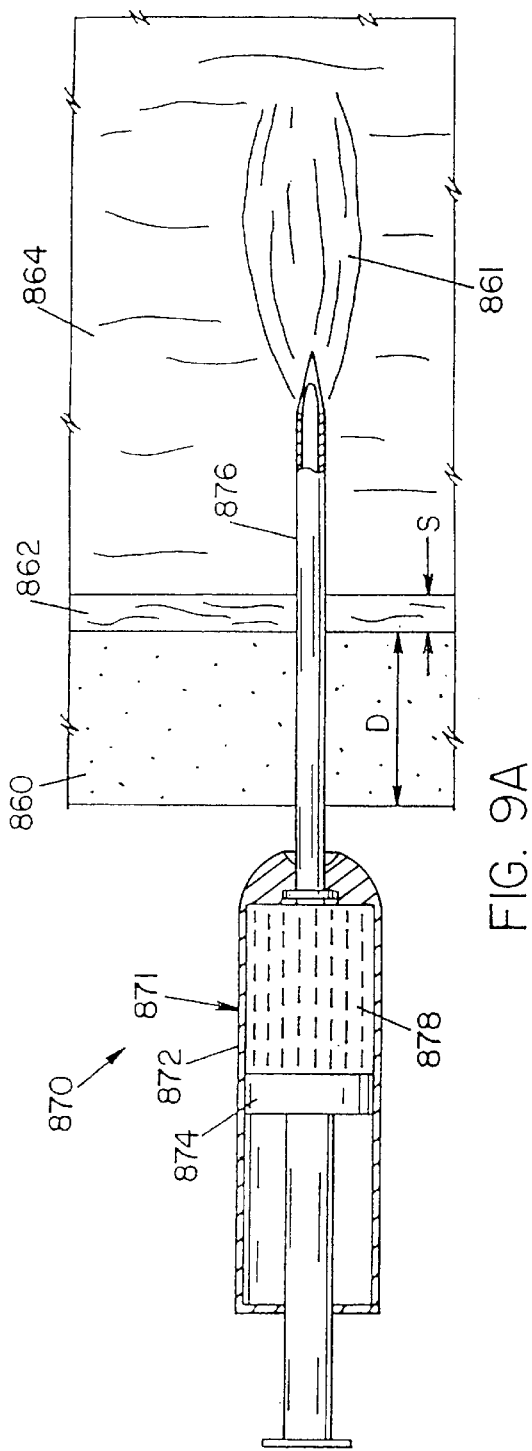
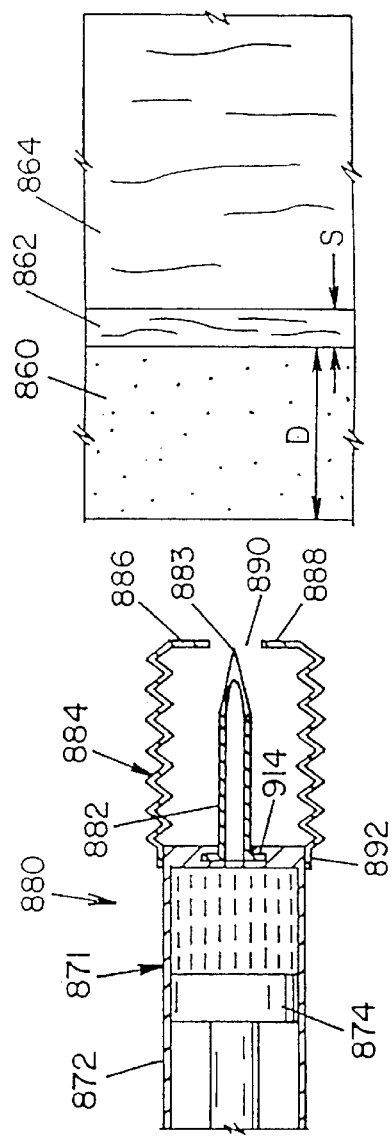
FIG. 9A (PRIOR ART)
FIG. 9B

HYPODERMIC FLUID DISPENSER

CROSS-REFERENCE TO RELATED APPLICATION

This application is a continuation-in-part of corresponding U.S. patent application Ser. No. 08/253,416, filed Jun. 3, 1994 now U.S. Pat. No. 5,569,190, which is a continuation-in-part of Ser. No. 07/818,235, filed Jan. 8, 1992 now U.S. Pat. No. 5,318,522, which is a continuation-in-part of Ser. No. 07/336,636, filed Apr. 7, 1989 now U.S. Pat. No. 5,080,648, which is a file wrapper continuation of U.S. Ser. No. 07/059,620, filed Jun. 8, 1987, now abandoned.

BACKGROUND OF THE INVENTION

1. Field of the Invention

This invention relates to apparatus for the hypodermic injection of fluids.

2. Description of the Prior Art

Hypodermic fluid dispensers fall into two broad categories, namely, needle hypodermic dispensers and needle-less injectors, such as jet injectors. In the past, jet injectors have been particularly useful in large scale immunization programs, such as those administered by the World Health Organization (WHO) or the military, for example, where the number of subjects to be immunized in a single session is very large (more than 200 injections per session). However, in recent years, jet injectors are also finding benefit in more routine immunizations at WHO health centers around the world, where the number of subjects injected is relatively small at less than 40 injections per session.

In general, jet inoculation, as compared to needle inoculation, is less traumatic, requires less operator training, and allows a higher number of procedures per unit of time.

Although both needle hypodermic injectors and high pressure jet injectors have been widely used, the presently known devices have serious disadvantages with respect to the injection of humans and animals alike. There exists a high level of belief that conventional jet injectors are capable of cross-infection when the same orifice is used for subsequent injections, and the problems associated with needle injectors in the spread of AIDS (Acquired Immune Deficiency Syndrome) alone is sufficient motivation to avoid proliferation of today's needle systems. People cannot be relied upon to dispose of needle injectors in accordance with instructions and good practice, and an element of the population are tempted to reuse needles without knowledge of or regard for safe practices.

There are other important shortcomings in the present state of the art with respect to the inoculation of humans and large animals, such as cattle and pigs. In the case of large animals, needles used for injecting vaccines, vitamins, medications and hormones in large, food-producing animals often cause damage to prime portions of the meat through the creation of abscesses and scars, resulting in serious economic loss to the industry. In the majority of cases, these factors are even more prevalent because the needle injectors become dull or bent when used for multiple injections, which is a common practice in the industry. In addition, due to increased awareness of cross-infection in food-producing animals, agricultural leaders recommend that needles no longer be reused for animal injections. Furthermore, it is not at all unusual for multiple injections to be scheduled within the same period of time, this being true for humans and animals as well. However, repeated injections are usually met with greater resistance by the recipient and also makes the procedure far more expensive. Hence, other important shortcomings would be overcome if more than one material could be injected at the same time.

Properly configured jet injectors provide the best chance for reducing the problems of cross-contamination, as well as the case where more than one injection is required at the same time, and could reduce the time to train people involved in the injection process. If jet injectors were effective for both animals and humans, a higher number of procedures per unit of time would be possible. The higher number of procedures is particularly important in the beef and dairy industry where each day a certain number of animals receive injections. This is also true for the multiple vaccine requirement for children.

Large animal hide, such as cowhide, can be very thick, often in the range of 1/8 inch to 3/8 inch or more in thickness. The hide includes the hair, a tough outer layer, and thereafter the dermis, whose inside surface has a rubber-like interface that begins the subcutaneous ("sub-Q") layer that separates the hide and the muscle. In cattle, injections are usually given in the neck, a leg or a hind quarter. A known $CO_2$-driven jet injector was experimentally tested on a freshly euthanized cow and the injection site was immediately followed by a pathologist's examination. It was found that the injection rarely penetrated the desired depth into the muscle.

Electrically operated needle-less injectors, previously disclosed, often require batteries, since standard power sources are not available at remote or isolated areas where injections are often given. People responsible for the immunization programs at these locations are concerned about disposal of these batteries, leading to the recommendation that rechargeable batteries be used. Indeed, the use of any electrically-powered injector used away from standard power sources would be enhanced if there were no batteries to be disposed of, yet sufficient electrical power were available.

The exit path of needle-less injectors, referred to as "orifices," present additional problems. Orifices are commonly found in the range of 0.004 to 0.014 inches. Extensive experimentation has shown that these orifices are likely to be ineffective for deep injections unless virtually perfect in structure and optimized in diameter for that particular injection site. If the orifices are poorly configured, they will fail to penetrate the thick hide of an animal, and satisfactory deep injections will not occur no matter what pressure is applied on the serum or other product being injected. When poorly configured orifices with diameters in tile range of 0.004 to 0.014 inches are used with injection pressures as high as 2,000 to 10,000 psi, effective deep injections have not been possible.

It is important that the speed at which needle-less injections are made is high, whereby the entire dose, or doses, enters the animal's body quickly by way of the high velocity jet stream. Movement could cause a loss of the initial penetration point and the injection could fail. As noted above with respect to cows, the injection must clear a hide thickness of 3/8 inch, or more in some cases, to achieve intramuscular ("IM") injection. Speed of injection, orifice size, quality of the jet stream, and lack of movement are necessary to get good IM injection results. If any of these characteristics are not fully met, or if the jet stream breaks down when the injection material is designed for an IM injection, the fluid will remain in the dermis, or in the subcutaneous layer instead, and could result in a less-effective or even a totally useless injection.

Presently known collapsible bodies or containers (generally referred to hereinafter as "containers") for holding hypodermic fluid do not readily provide the necessary fluid even when sufficient pressure is applied to the collapsible container. Collapsible containers do not exist for effecting the proper mixing of ingredients at the time sufficient pressure is applied to the collapsible container.

Present needle-less jet injector systems are very expensive. For one thing, these systems draw the serum or other injecting fluid into disposable capsules having walls thick enough to withstand the high pressures of about 1,700 psi or more for human IM injections.

Another problem with jet injector systems is that they "gum up" from the injectant material if the user fails to thoroughly clean the device on a timely basis. In some situations, such as field use with cattle, this procedure is difficult, if not impossible, in terms of available time and equipment.

Some injection fluids have higher viscosities than water, such as the BST growth hormone, Posilac, for enhancing milk production. If the fluid becomes too viscous because of lower temperatures, proper injection would not be possible. Presently, no temperature measuring systems for injection fluids are available.

SUMMARY OF THE INVENTION

It is an object of the present invention to provide an improved injection system for injecting materials such as vaccines, sera, growth hormones, vitamins, nutrients, and the like into a living body.

It is another object of the invention to provide a system for injecting material of the foregoing type into a body to obtain an effective injection even though the body may move somewhat during the injection process.

Yet another object of the invention is to provide a system for effectively injecting materials of the foregoing type through thick outer layers of a body and evenly disbursing the fluid from a high velocity, piercing jet stream at the inner regions in the event this is the desired target area.

It is a more particular object of the present invention to provide an injection system for injecting material of the foregoing type into large animals, such as cattle, having thick hides.

Another object is to provide an improved collapsible container or containers for holding material to be injected into an animal or person, once sufficient pressure is applied to the collapsible container or containers.

Yet another object is to provide an improved collapsible container or containers for holding injectant material which can bring together different ingredients to be injected once sufficient pressure is applied to the collapsible container or containers.

It is still another object to provide a jet injection system for injecting the foregoing types of materials into animal and human bodies having low-cost capsules with thin-walled cavities for holding the material to be injected.

Another object is to provide an effective injection system having multiple orifices for effectively reducing the time required for injecting a larger dose of material into animals and humans or for injecting multiple products at the same time.

Another object is to provide means to deposit each of the multiple products at different locations and/or at different injection depths.

It is still another object to provide means to inhibit injection site pain for the injection of singular or multiple products.

Another object is to provide electrical stimulation to dull injection site pain.

A further object is the provision of an injection system for preventing actuation of the system until certain conditions are met.

Another related object is to provide an injection system having a trigger which is actuable only when an anti-splash guard ring is properly in contact with the surface through which the injection is to be made.

Another object of the invention is to automatically provide an injection site mark or legend as an indicator that a group of animals or humans have already received a particular injection.

It is an additional object to prevent the unauthorized use of an injection apparatus.

Another more particular object is to provide an injection system having a trigger which is actuable only when an access code is first keyed into the system.

It is yet another object of the invention to provide a jet injection system having a hybrid needle/orifice combination which is designed to proceed through the outer layer of a body and obtain a more effective dispersion of the injectant material at a preferred injection site.

A further object is the provision of a hybrid/orifice combination jet injection system for animals which is so constructed that the system will not be impaired even if the animal moves during the injection process.

It is also an object of the present invention to provide an injection system having batteries or a storage capacitor which can be recharged with solar energy.

Another object of the invention is to provide a solar powered jet injection system and a solar generator for powering the jet injector at remote locations away from access to central electric power supplies.

Another object is to provide a light weight, easy to handle, injection system to allow for injections at a significant distance from an animal when close proximity is difficult to realize.

It is still another object of the present invention to provide a robotic injection system for the automatic injection of subjects such as the living bodies of humans and animals.

An additional object of the present invention is to provide an injection system with a replaceable component for connecting the system to a reservoir.

A further and related object is the provision of an injection system with a replaceable component for connection to an injection chamber and integral orifice.

Another object is to provide an injection system for mixing lyophilized ingredients at the time of an injection.

It is yet another object of the present invention to provide an injection system having a replaceable exit channel, orifice device, and/or a replaceable needle device, used in connection with a permanent medication chamber.

It is still a further object of the present invention to provide a temperature monitor for measuring the temperature of materials to be injected.

Another related object is the provision of a temperature monitoring device for an injection system for disabling the injection system if the temperature drops below threshold value(s).

A general object of the present invention is to provide an efficient, effective, yet economical system for injecting animals and people.

Other objects will become apparent from the description to follow and from the appended claims.

One form of the present invention makes possible the quick completion of the injection process through the hide of an animal. This form comprises a short perforating member with a jet system for forcing an injecting fluid under high pressure through the perforating member. Depending on the location of the injection, the perforating member of this hybrid combination is from $\frac{1}{8}$ to $\frac{3}{8}$ inch or more in length and is surgically sharp with a slanted point for easy insertion. When the perforating member is pressed into the hide of an animal, it creates an anchor point therefore eliminating the detrimental risk of movement by either the person making the injection or by the animal. The high pressure, high velocity jet stream from this vantage point is not deflected by the hair on the hide or the tough outer layer so that the jet flow remains coherent. The sharp, slanted needle point moves the debris aside rather than forcing it into the hide. Since the perforating portion of the hybrid combination extends through the hide, less injection pressure is necessary to reach the subcutaneous layer or intramuscular region of the animal if this is the injection site of choice. Consequently, lower motor torque is required, thereby allowing for a smaller power source for an equal number of shots than required by prior art systems. In addition, the orifice portion of the hybrid combination can be increased in size to provide for a faster discharge of the injection material thus allowing for larger doses with the same injection time. The lower cost motor and power source, along with a smaller and lighter weight for the system render it more economical and easier to use.

Because of the low cost, the hybrid perforator/orifice combination can be discarded after each use, further eliminating cross-contamination. Another embodiment of the invention incorporates a protective containment chamber into which the hybrid perforator can be withdrawn after the injection is completed, making the needle portion inaccessible for subsequent reuse, providing yet another way for preventing cross-contamination. When a jet injection is given through the perforating member, the orifice portion of the combination generates a coherent, evenly dispersed jet stream without having the needle portion penetrate the muscle, and thereby avoid the large economic loss in the meat industry from prior art needle injections.

Another aspect of the present invention is the provision of a collapsible container for holding one or more materials to be injected, having a needle device for injecting the material once collapsing pressure is applied to the container to force the materials from the container.

A further version of the invention is the provision of a collapsible container for a hypodermic system having holding containers or reservoirs (hereinafter generally referred to as "reservoirs") for ingredients to be combined for injection, and a needle device for penetrating a reservoir when sufficient pressure is applied to the collapsible container to cause the ingredients to be combined.

Another form of the present invention enables the use of low-cost, thin-walled capsules for holding the materials to be injected, even though the capsules must be able to withstand pressures commonly used with jet injection procedures. According to this version of the invention, the thin-walled capsule is held in a restraining structure, similar to a gun barrel, which serves to protect the capsule from expanding, bursting, or even leaking, as a result of the high pressure. The use of a restraining structure with a thin-walled capsule enables the mass immunization of animals and humans at a cost no greater than that experienced with conventional needle/syringe systems, but without all of the risks associated with needles. A restraining structure and thin-walled capsule eliminates the requirement for conventional needle injections and also eliminates the high cost of the thick-walled capsule of prior art systems. The hybrid perforator/orifice concept can also be used with the restraining structure and thin-walled capsule for higher pressure injections into thick hided animals, thus realizing an economical approach for this application as well.

Another aspect of the present invention is a jet injector system with multiple orifices for enabling fast injections of high doses of injecting material than heretofore possible. The number of orifices generally equals the number of times faster that an injection can be made. Multiple orifices could be used in human surgery, such as for plastic surgery where a fairly large surface pattern must be anesthetized, or in combination with multiple capsules to administer more than one serum product simultaneously at adjacent points of entry and, if advantageous, to further discourage the mixing of products at the injection site by providing for different injection depths for each product at each point of entry.

To better suppress the possibility of pain, another aspect of the invention provides for electrical stimulation to desensitize the injection site. This technique is especially useful with the added risk of pain due to multiple, simultaneous points of entry with either high velocity jet streams or needles.

Still another version of the present invention disables the actuation of the inventive system until additional predetermined conditions are met. An embodiment of this version includes a second switch in series with the actuating member such as a trigger.

In order to eliminate the battery disposal problem which could accompany battery-powered jet injection systems at remote locations, another embodiment of the present invention utilizes methods of energizing the low power requirements of an electrical injector. One version of this embodiment incorporates a relatively small gel cell or fluid electrolyte battery connected to a single injector or multiple injectors with light weight, low cost extension wires. For example, multiple injectors could be operated at the same time at remote health centers dealing with epidemic immunization requirements. The power sources for the injectors would be rechargeable directly from the transport vehicles if available. Such recharging can also come from an inexpensive low-power solar charger or directly driven with a solar generator of greater capacity. These recharging systems pursuant to the invention can eliminate the need for grid power or the more expensive and generally unwieldy electrical generators, carbon dioxide tanks, hydraulics and breakable foot pedals.

Another version of the invention is a robotic system. Herds of cattle ordinarily pass through separating chutes when they enter the barn. Animals to be injected can be electronically identified and separated from the herd. Such an identification could be by means of tags with bar codes. The separated animals could be restrained, and a long arm of a robotically-operated jet injector would inject the restrained animals and then release them when completed, pursuant to this version of the invention.

In a related version to the long arm of the robotic system, a long-armed manual system is provided with the injection mechanism and a surface contact enabling head at the target end and an actuating trigger at the user end. This embodiment has utility for the injection of large animals such as pigs, since getting close to the animal is sometimes difficult and/or inconvenient. Such a system could allow for removal of the robotic arm and use in the manual mode. The extended arm concept can be provided as a totally independent manual system.

Another aspect of the present invention comprises an automatic marking system. The automatic marking system is used with respect to large numbers of animals or humans in close proximity to each other. The system includes a nozzle adjacent to the injection nozzle. The marking system automatically marks the subject when an injection is given. The marker, which should be a non-toxic dye, is preferably such that its expected life does not exceed the time between injections. Different indicia, such as using more than one color of the dye, will make multiple injections distinguishable. In this way, the user is able to tell which of the animals and/or humans in a large, close proximity group have already been injected with a particular product so that none are missed and none are injected more than once.

Another version of the present invention involves the elimination of the "gumming-up" which frequently affects jet injectors if the user fails to clean the device on a timely basis. According to this version of the invention, the jet injector gun has, as an integral unit for each serum to be administered, a tube for connection to the reservoir having the injectant material, a chamber and an orifice, which is inserted into the gun as a single composite system containing all of the elements necessary for delivering one or more serums at the same time. During a series of shots, the injectant fluid or fluids are drawn into the chamber or chambers and injections are given through the integrated orifice system. At the completion of the entire series of shots, the integral unit is removed and discarded. Only the removable and disposable integral unit contacts any injection fluid; the gun itself does not contact any fluid and does not gum-up. The system could be used with a single-shot disposable orifice and perforator for each fluid to eliminate cross-contamination.

BRIEF DESCRIPTION OF THE DRAWINGS

The invention is illustrated in the accompanying drawing in which:

FIG. 7CC is a pictorial view of the embodiment shown in FIG. 7C in use;

FIG. 7GG is a pictorial illustration of another embodiment of the invention showing multiple independent injection chambers each having its own exit orifice;

FIG. 7GG' is a detailed, pictorial view of a single injection chamber and exit orifice from the multiple chambered system of FIG. 7GG;

FIG. 9A is a schematic showing the "pooling" effect when the injectant is introduced into the injection site using the prior art needle and syringe occurring after an injection;

FIG. 9BB is a side view of a perforator with a slanted tip according to an embodiment of the invention;

DETAILED DESCRIPTION OF THE EMBODIMENT

Figures 1, 2A, 2B:
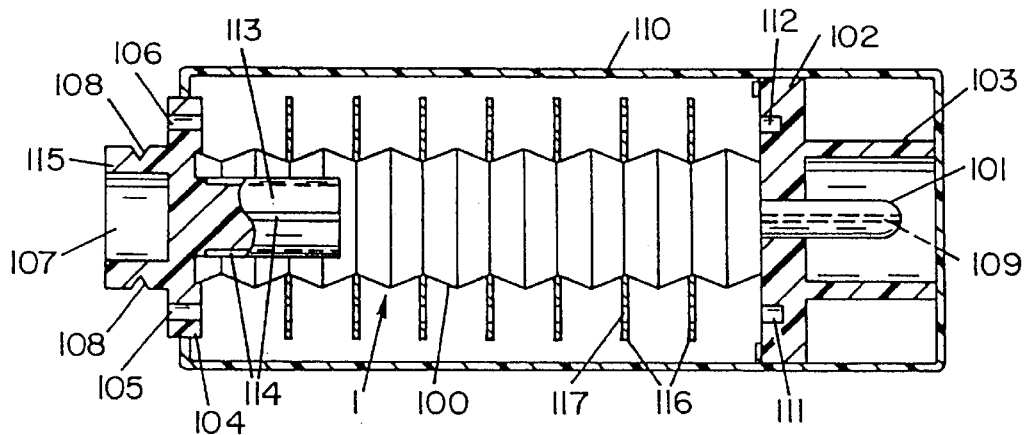
FIGS. 1 and 1A illustrate side, cross-sectional views of two multiple inoculation jet injectors in accordance with the invention.
FIGS. 2A and 2AA illustrate cross-sectional views of jet injector systems with the fresh injectors of FIGS. 1 and 1A, respectively, installed therein.
FIGS. 2B and 2BB illustrate side, cross-sectional views of the jet injector systems of FIGS. 2A and 2AA, respectively, with the injectors partially expended.

FIG. 1 illustrates a liquid filled jet injector or dispenser 1 stored in a protective cover 110. The jet injector of FIG. 1 comprises a liquid-filled bellows 100; a front plate 102 which comprises a pair of guide rod recesses 111 and 112, a set of thin washers 116 which have an inner diameter slightly larger than the minor diameter of bellows 100, a pair of holes 117 in each of the washers 116 that are aligned with the guide rod recesses 111 and 112 and with the openings 105 and 106; a spacing guard ring 103, with an interrupted pattern 901 shown in FIG. 1B to prevent sliding between the dispenser and the skin; a disposable and replaceable exit nozzle 101 with an output port 109 (shown in greater detail in FIG. 1C); a ram 113 with a groove 114; and a back plate 104. Guard ring 103 can advantageously have the features shown in FIGS. 1B and 1C, respectively. An interrupted pattern 901 at the end of ring 103 in FIG. 1B prevents sliding between the dispenser and the skin of the person being injected. The nozzle 101 has its end 903 threaded in FIG. 1C or the like so that it can be disposable and replaced. The back plate 104 comprises openings 105 and 106, aligned with holes 117 in washers 116, which accept a pair of guide rods when the jet injector cartridge is installed in the system of FIGS. 2A and 2B; and a ring 115 which forms the recess 107 for receiving a drive spring 227 of the system of FIG. 2A. The injector of FIG. 1 may be a disposable injector or a multitude of permanent reusable injectors for the administration of, for example, the growth hormone. The attendant can pre-fill a multitude of the cartridges shown in FIG. 1A carrying them in a belt holster, or as shown in FIGS. 7C and 7D, in a single large container or sack with a hose connected to the injection chamber. The output port can be made of ceramic, plastic, glass or metal and may be removable and replaceable or a permanent part of the injection head. In either case, device economy is improved by fabricating a molded output port having tile flow orifice formed by first inserting a preformed metal, or other sufficiently sturdy member, whose size and shape, i.e., length, diameter and flow path angilation are chosen to provide laminar flow. Some of the other possible methods for forming the orifice include laser boring, water jet cutting and electron beam cutting.

FIG. 2A is a cross-sectional representation of an illustrative embodiment of a hypodermic jet injector system with a fresh jet injector of FIG. 1 installed therein. The system of FIG. 2 in general comprises: a housing 220; the control, monitoring and display arrangements of FIGS. 3 and 4 (not shown in FIG. 2A); an electric drive motor 221; a motor output shaft 222 with a threaded portion 223; a loading ram 224 with internal threads 225 which mate with the threads 223; an energy storage spring 227; a reluctance transducer shield 226 to be described with respect to FIG. 3 later herein; a pair of guide rods 228 and 229 that serve to align and support the bellows 100; retaining latches 238 and 239; and a trigger mechanism which comprises the detents 232 and 233, the follower springs 230 and 231 and the follower blocks 234 and 235. The mechanism for releasing the detents 232 and 233 is not shown in FIG. 2 and any suitable mechanical linkage which effects the simultaneous lifting of the detents 232 and 233 is satisfactory. In an alternative mechanical embodiment for loading energy storage spring 227, threaded motor shaft 222 is replaced with a shaft driven cam which serves to compress energy storage spring 227 as the motor shaft rotates.

Figure 1A:
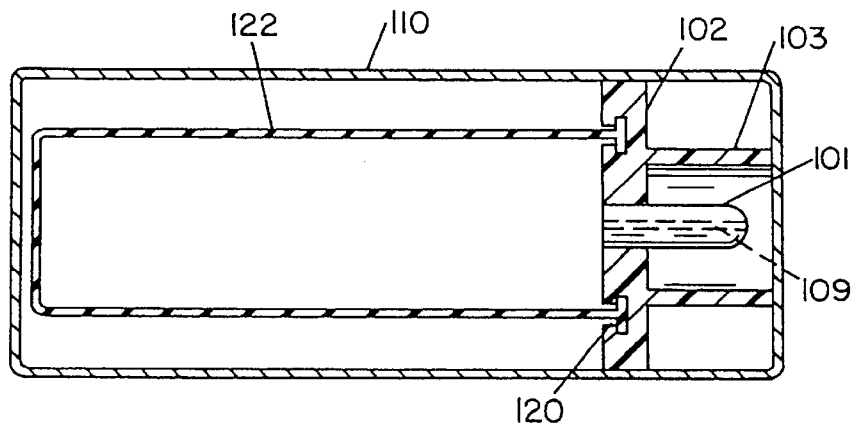
Figure 2A:
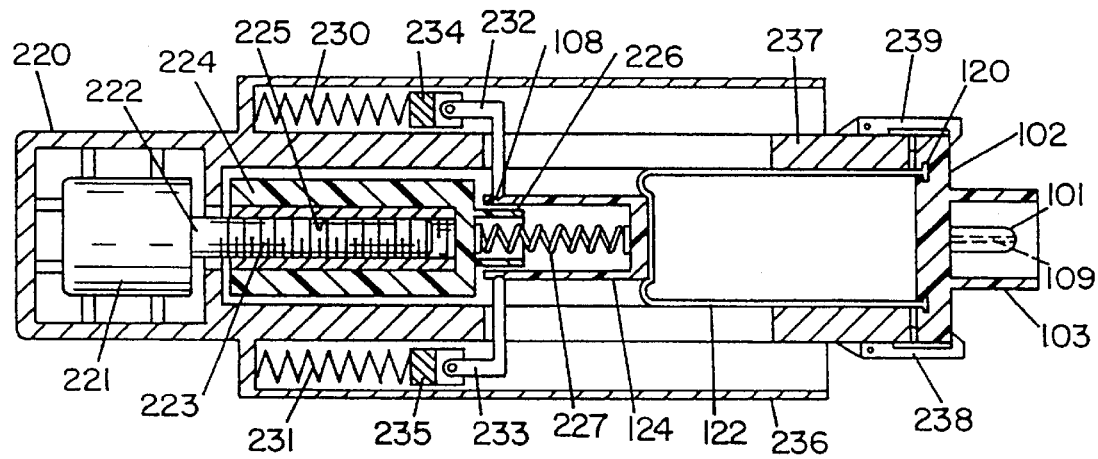
Figure 2B:
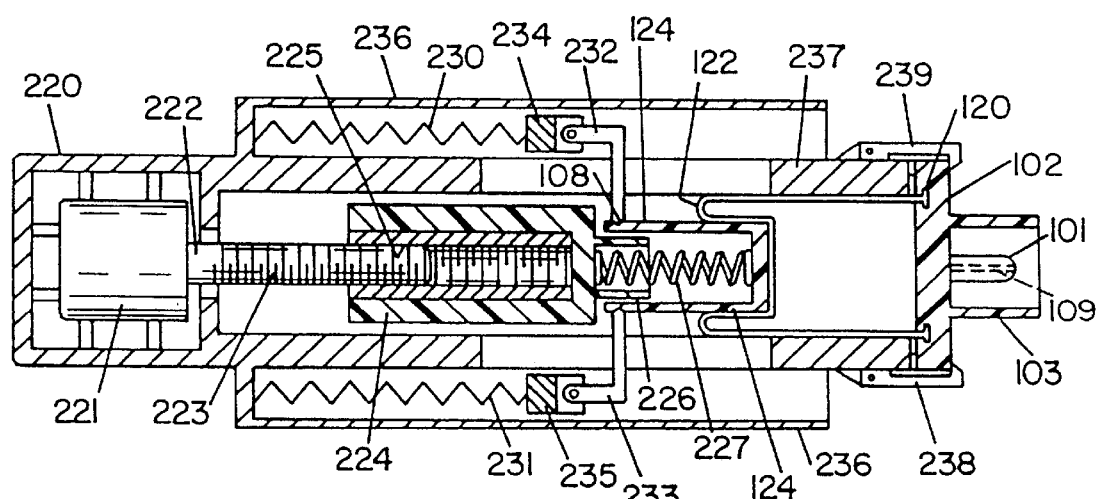
Figure 1B:
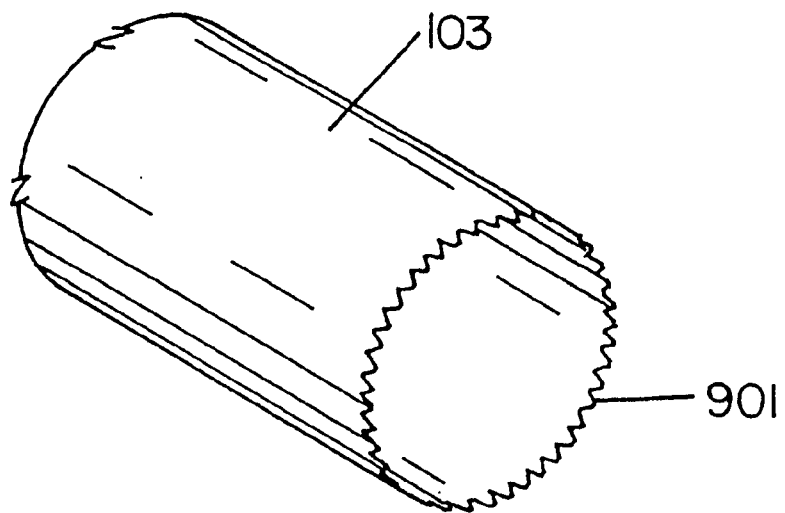
FIG. 1B is a partial pictorial view of a modified body ring guard for use in the injectors of FIGS. 1 and 1A.
Figure 1C:
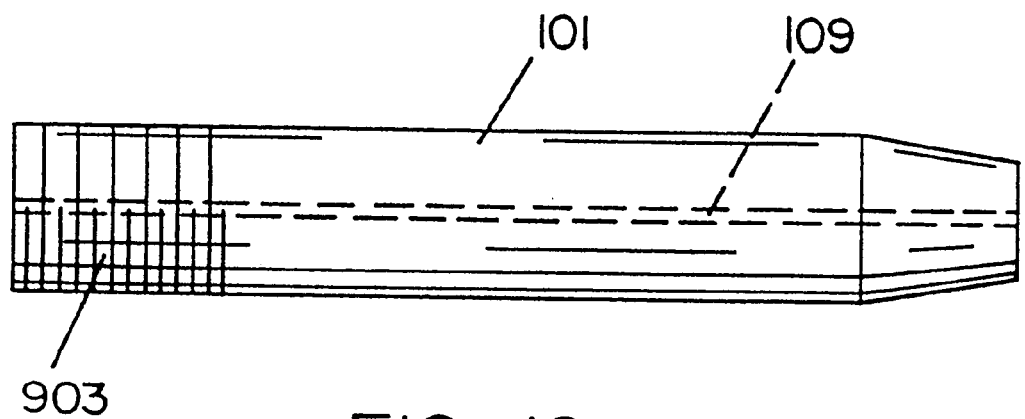
FIG. 1C is a pictorial view of a modified nozzle for use in the injectors of FIGS. 1A and 1B.

An alternate embodiment of the injector of FIGS. 1, 2A and 2B is illustrated in FIGS. 1A, 2AA, and 2BB. In the alternate embodiment, the liquid-filled bellows 100 is replaced by a collapsible liquid-filled "hat" diaphragm-type structure. Detents 111 and 112 of FIG. 1 are replaced in FIG. 1A by slot 120 for mounting and firmly securing hat structure 122 to the front plate 102. This arrangement is equally effective if the fluid chamber is replaced by a piston-type syringe.

FIG. 2AA is a cross-sectional representation of the injector system with a fresh injector installed therein. When the diaphragm 122 is inserted in the now conformal housing 220, a slight initial collapse of 122 occurs to facilitate chamber venting and to assure an effective inner folding action as the multiple injections follow. The conformal shape of housing 220 constrains fluid chamber 122 and thus prevents undesired outward expansion under the influence of the injection pressure when the spring 227 is released. Back plate 124 is configured to assure that the detents 232 and 233 do not interfere with fluid chamber 122 as it progressively folds inside its outside diameter (FIG. 2BB) with each additional injection. In the case of the syringe, the piston is progressively pushed to the right as the injections occur.

While the following discussion is specific to the embodiment of FIGS. 1, 2A and 2B, the discussion applies equally to the alternate embodiment of FIGS. 1A, 2AA and 2BB and the piston-type syringe dispenser.

Figure 3:
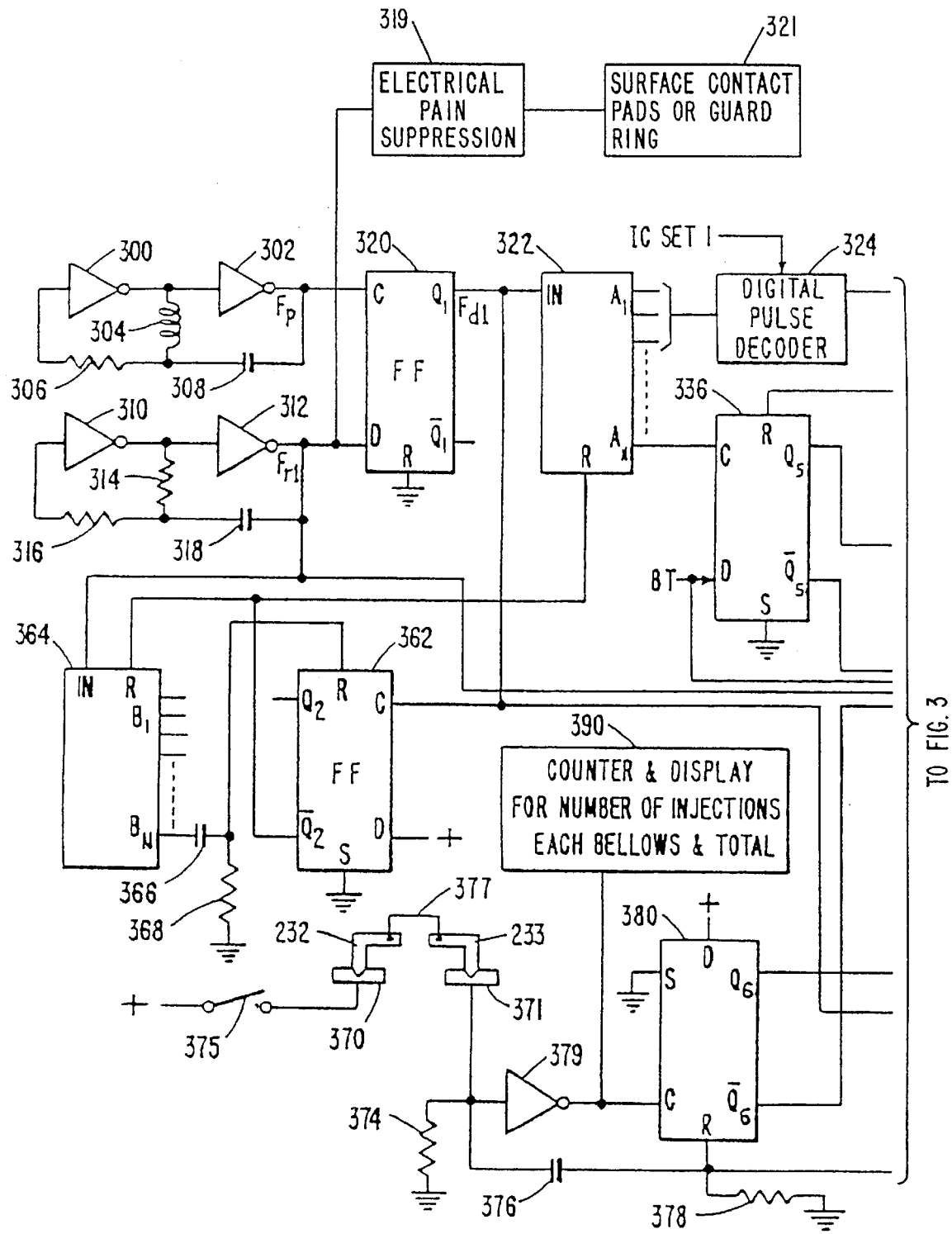
FIG. 3 and FIG. 4 are schematic representations of one embodiment of the control, monitoring, and motor drive circuitry of the jet injector system of FIGS. 2 or 7.
Figure 3:
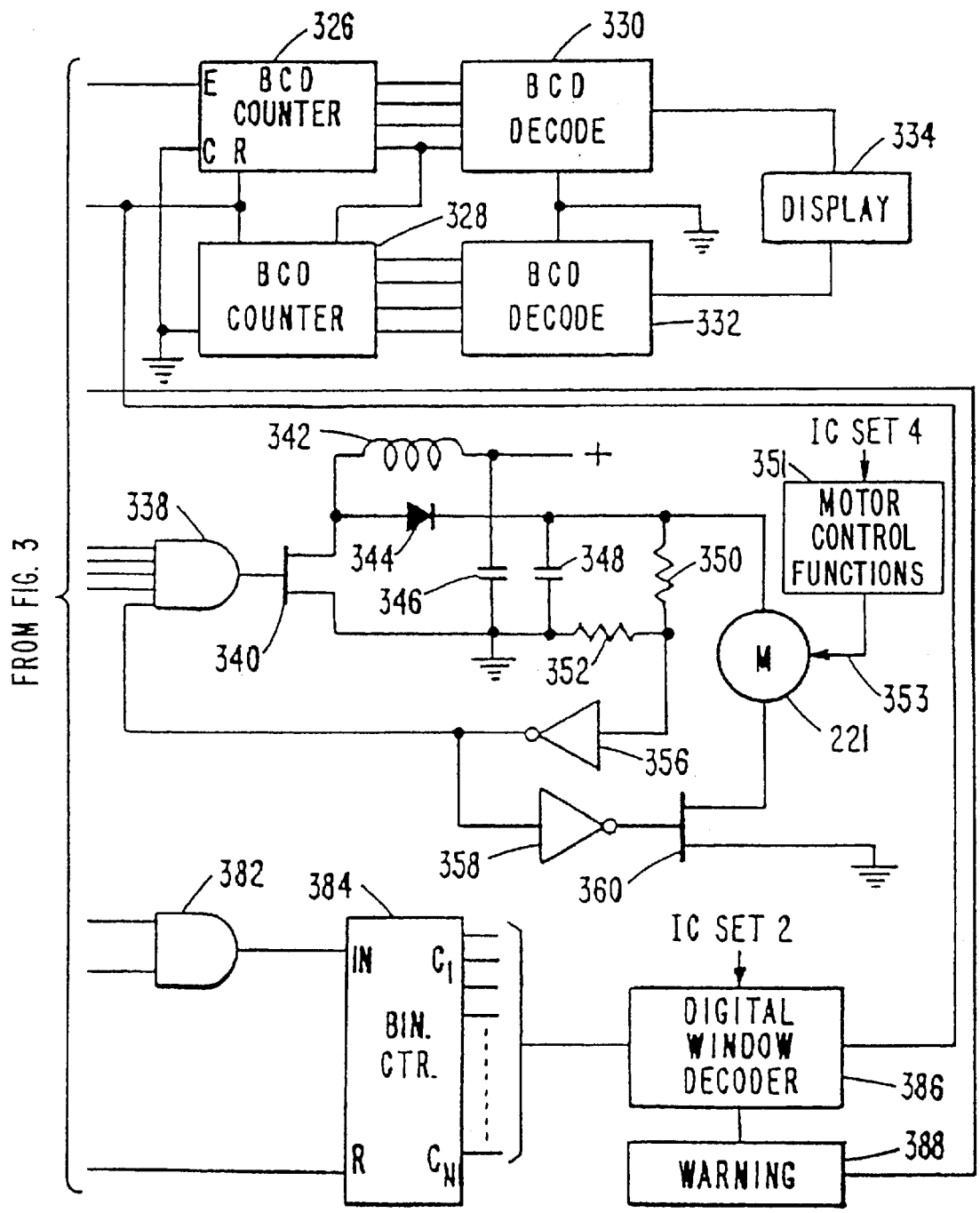
Figure 4:
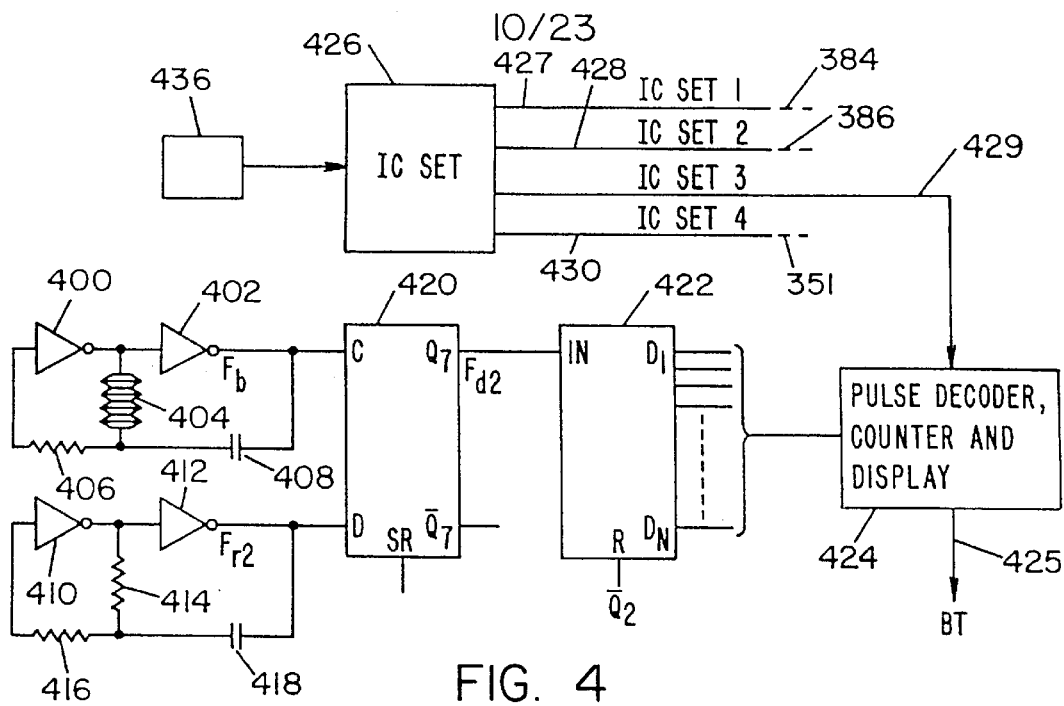

Prior to the time that a fresh jet injector of FIG. 1 is installed in the system of FIG. 2, a manually operable reset switch 436 of FIG. 4 is operated to enable the IC Set circuit 426 of FIG. 4 to establish initial system conditions. The output signal of the circuit 426 enables motor control functions 351 of FIG. 3 to draw the loading ram 224 back into the initial position illustrated in FIG. 2A or to rotate the cam to its starting position; output signal 427 initializes the digital pulse decoder 324; output signal 428 is transmitted to the digital window decoder 386; and signal 429 is transmitted to the pulse decoder, counter, and display 424. Alternatively, the ram 224 or the cam can be manually returned to the initial position at the time that a fresh bellows is installed.

The functions of the pulse decoder 324, the window decoder 386 and the pulse decoder counter and display 424 will be apparent from the description of FIGS. 3 and 4 which appears later herein. After the system is thus conditioned, a fresh jet injector is removed from the protective cover 110 and inserted into the housing 220 as illustrated in FIG. 2A. To install the jet injector, the guide rods 228 and 229 are inserted into the openings 105 and 106 in the back plate 104, through the openings 117 in the washers 116, and the injector is moved into the housing 220 until the front face of the front plate 102 is clamped by the latches 238 and 239. As the jet injector is moved into the housing 220, the detents 232 and 233 engage the notches 108 in the back plate 104 and follow the motion of the back plate as it is moved to the left in FIG. 2A. The follower blocks 234 and 235 follow the motion of the detents 232 and 233 to the left and thus compress the follower coil springs 230 and 231. Further, when a fresh injector is in position as illustrated in FIG. 2A, the energy storage spring 227 enters the recess 107 in the back side of the back plate 104. The system of FIG. 2A is in condition for an operator to perform a series of inoculations.

Figure 2C:
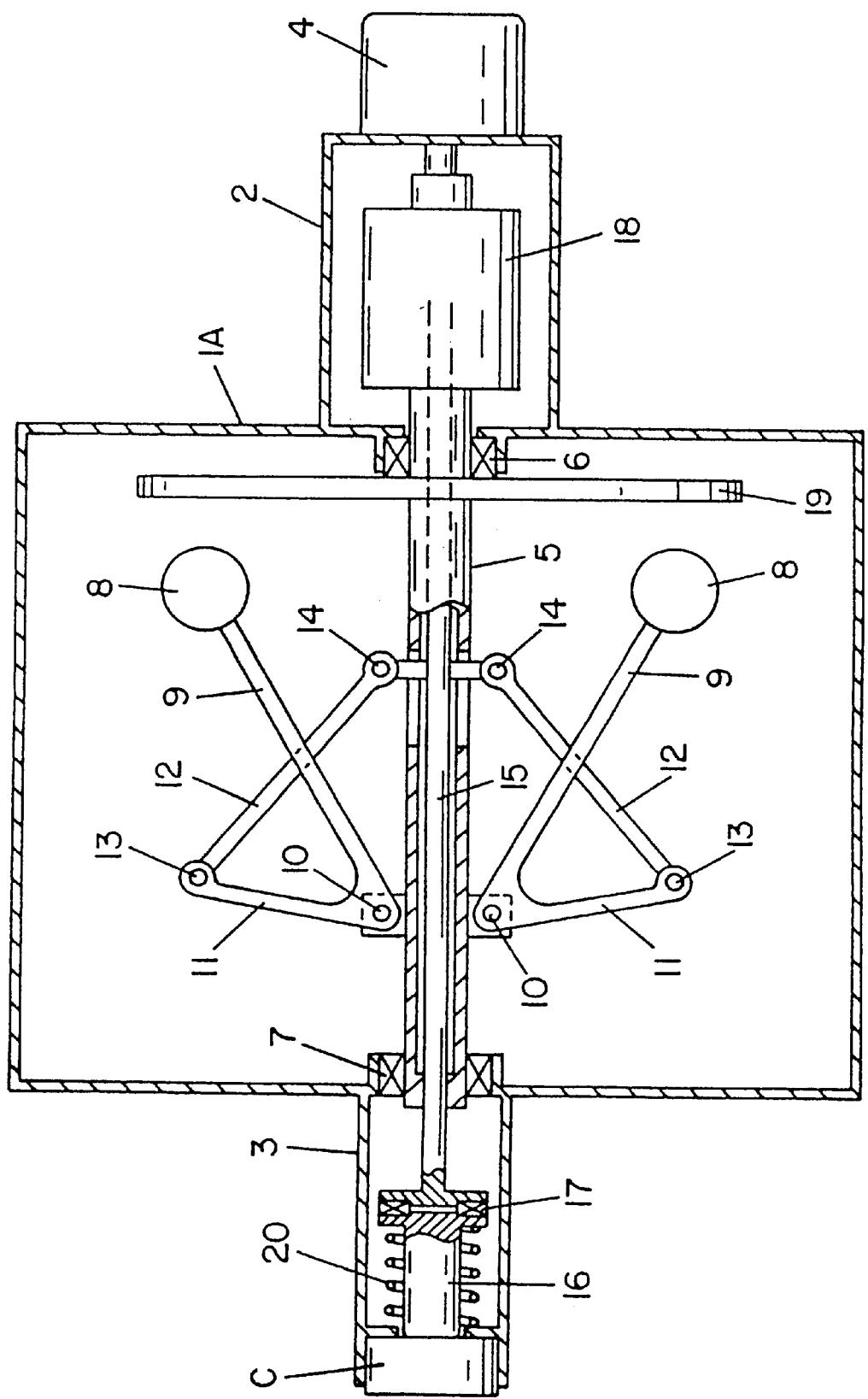
FIG. 2C is a schematic diagram illustrating a fly-wheel system as an alternative to the spring of FIG. 2A, 2AA, 2B and 2BB for producing injection pressure.

Under operator control, the system of FIGS. 2A, 3 and 4 selectively provides power to the motor 221 to advance the ram 224 to the right in FIG. 2A and thus compress the coil spring 227. As described later herein, the circuitry of FIG. 3 monitors the degree of compression of the spring 227 and removes power from the motor when the compression reaches a target value or when the selected flywheel speed of FIG. 2C is reached. The target value is either a default value established by the manufacturer or a value established by an operator on the basis of experience. After the spring has been compressed or motor speed reaches the target value, the guard 103 is held perpendicular to and against the skin at a suitable site of a subject to be injected. The outer ring surface of guard 103 may have a tooth-like pattern 901 to reduce the possibility of the ring sliding along the skin during the course of an injection. Guard ring 103 can also contain electrical pain suppression contacts. If the ring does slide during the injection the subject may receive a "jet cut" rather than a jet inoculation. The operator initiates injection by depressing a trigger, which as indicated earlier herein is not shown in the drawing. Depression of the trigger simultaneously releases the detents 232 and 233 from the recesses 108 in the back plate 104. The energy stored in the spring 227 is released and the back plate 104 is rapidly driven to partially collapse the bellows 100. As the bellows is collapsed, a desired amount of fluid is driven through the output port 109 in the projection 101. Advantageously, the use of a compressed spring as a source of energy provides a high initial pressure which reduces as the bellows 100 collapses. The size and the length of the port 109 and the pressure profile supplied by the compressed spring projects the fluid with a desired pressure profile which assures hypodermic injection of the fluid to the desired depth. The diameter and the length of the port 109 are chosen to assure laminar flow of the fluid from the chamber to the output tip. As the bellows collapse, guide washers 116 move together and prevent the bellows from bending under the influence of the high initial force of the injection.

As explained earlier herein, when a fresh injector is inserted into the housing 220, the follower springs 230 and 231 are compressed. Therefore, after the trigger is released, the follower blocks 234 and 235 and the detents 232 and 233 are driven to the right in FIG. 2A until the detents again engage the corresponding recesses 108 in the back plate 104. The follower blocks 234 and 235 may be connected to a small dashpot if a delay in this action is desired. The system of FIG. 2A is then again ready for the operator to initiate another injection.

Because the wall of the bellows 100 has a finite thickness, a fully collapsed bellows has a substantial length. The length of the ram 113 approximates the length of the collapsed bellows. Without the ram 113, valuable fluid is left in a fully collapsed bellows. The groove 114 in the ram 113 prevents the trapping of fluid in the portions of the bellows which surround the ram 113.

Two additional alternatives to spring 227 can provide the pressure needed to give an effective injection. The first is a motor-generator in combination with an energy storage flywheel as shown in FIG. 2C. This embodiment represents a device for another method of intermediate energy storage when the power source is insufficient for a direct drive injection, and is especially useful for realizing a compact, lightweight design, even when a much higher pressure is required for an effective injection. In the second embodiment shown in FIG. 2D, injection pressure is developed directly from the motor with no intermediate storage of energy, such as a spring, compression chamber or flywheel. However, if applicable, an energy storage flywheel could be advantageously used with the drive mechanism shown.

The components of one version of a flywheel system of FIG. 2C are the housing 1 for the flywheel with rear extension 2 and front extension 3 to enclose the other moving parts. A motor 4 capable of accelerating to high speeds directly drives a spindle 5 rotating in a rear bearing 6 and a front bearing 7. At least two flyweights 8 swing on arms 9 on a set of pivot bearings 10 fastened to spindle 5. Arms 11 are rigidly attached to arms 9 and the flyweights 8. The centrifugal load of flyweights 8 is transmitted from arms 11 to a pair of links 12 through a pair of pivot bearings 13, then through a pair of pivot bearings 14 to a thrust rod 15. Rod 15 rotates with the spindle 5, and moves axially to the left in FIG. 2C as the radial distance of the flyweights from the central axis increases. The thrust load is transmitted to a plunger or ram 16 which moves axially without rotating and provides the force required for operating an injection device. Thrust bearing 17 is therefore required for transmitting the load from rod 15 to plunger 16. Plunger 16 transmits a pressure or load to a container C to effect the discharge of an injectant as a jet stream.

Figure 2D:
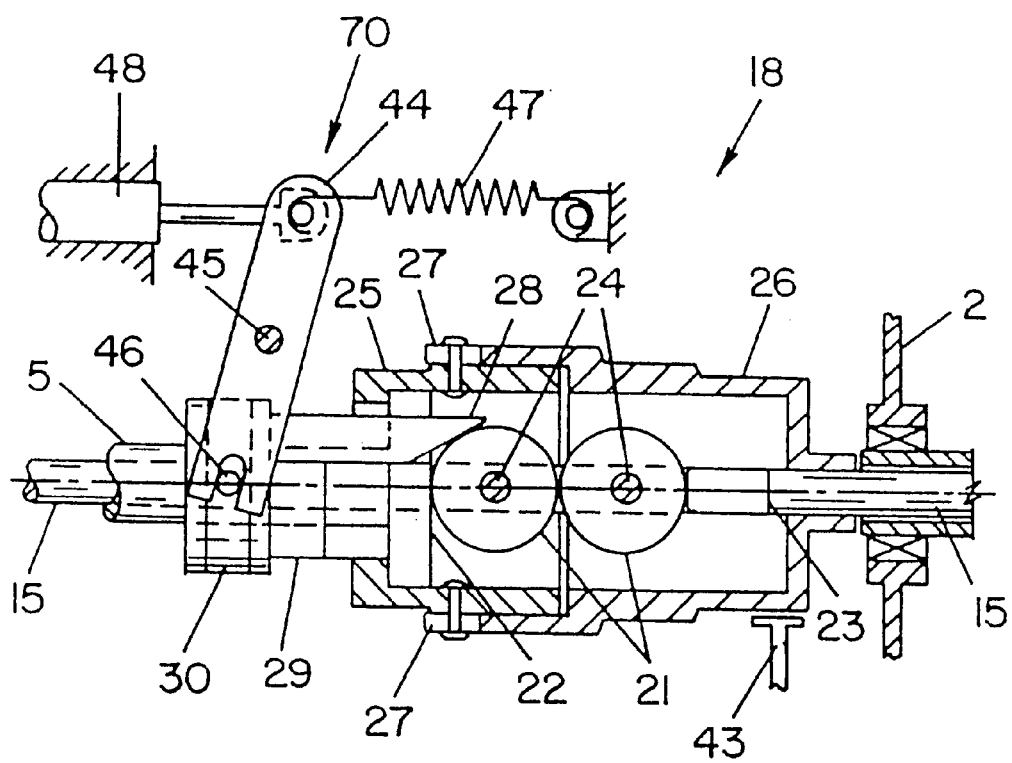
FIG. 2D shows a cross-section of a mechanical latch when the flyweights of FIG. 2C are in the most inward position.

The reaction from thrust bearing 17 is exerted at bearing 6, which must have a thrust capability equal to that of thrust bearing 17. Ball or roller bearings, which can be used for these bearings, should have very low friction, but the energy loss can be substantial because of the high loads and speeds. A rotating latching device 18 which locks all of the rotating parts together can eliminate the thrust load losses during acceleration. The latch could operate directly on the flyweights or could latch thrust rod 15 to the spindle, as indicated in FIG. 2D.

A constant-inertia wheel or flywheel 19 can be added for storing additional energy during acceleration that would compensate for thrust bearing and other losses during the injection phase, after latch release.

A light spring 20 restores the mechanism to the initial position after injection. It may be desirable to apply electrical or mechanical braking to stop flywheel rotation after injection. The energy loss from braking will be small since the speed is already greatly reduced.

The magnitude and variation of inertia, the characteristics of the flyweight-thrust rod linkage mechanism and the friction losses affect the force variations during injection. The linkage shown has an increasing mechanical advantage as the flyweights move outwardly, partially offsetting the decrease in centrifugal force from the speed drop caused by the increase in the moment of inertia and by the friction losses.

Figure 2E:
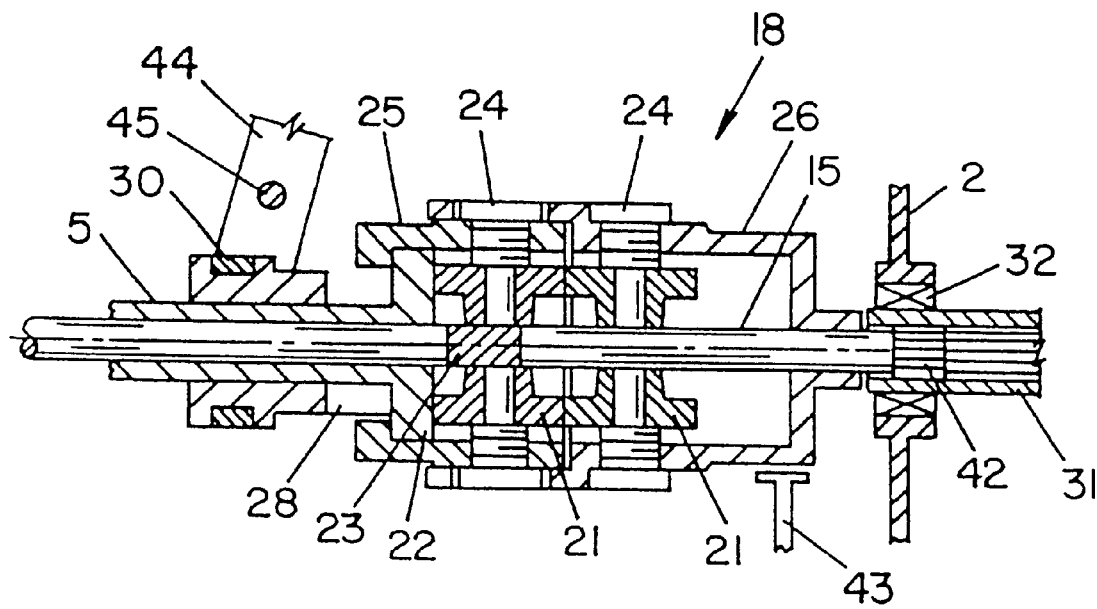
FIG. 2E shows the latch of FIG. 2D in final release, when the flyweights are in the most outward position.
Figure 2F:
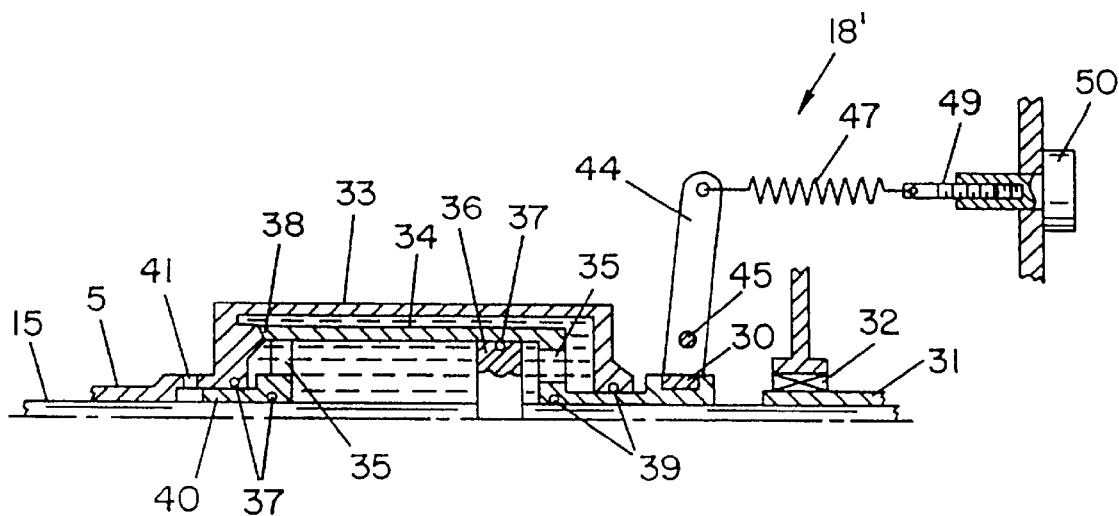
FIG. 2F shows a rotating hydraulic latch in the locked position.

FIGS. 2D, 2E and 2F show rotating latch designs. However, many parts required for assembly are not shown as individual items for reasons of clarity. While these figures are directed to a particular design concept, it should be noted that numerous methods of mechanical, hydraulic, magnetic and electrical latching systems are applicable. For example, release of the hydraulic latch of FIG. 2F can be facilitated with a variable force spring, wherein, as the motor accelerates to reach the selected speed, centrifugal force will increase accordingly. When centrifugal force finally exceeds the holding force of the variable tension spring, the latch will release. In another centrifugal force embodiment, the spring is replaced by holding magnets or, as an alternative, the flyweights themselves are magnetically held. In this case, break-away will occur when centrifugal force exceeds the holding force of the magnets. A variable holding force with the magnets can be achieved by changing the amount of overlap between the magnet face and the metal plate to which it is attached.

One embodiment of an electrical release that is applicable to FIGS. 2D and 2E utilizes a motor tachometer. In this case, the user will dial or key into the system the desired injection pressure, that is, motor RPM. When the target speed is achieved, an electrical signal is emitted to actuate a solenoid. Alternatively, a coil would around one or more holding magnets could be energized to momentarily reduce the holding force and a release will occur. Using an RPM dependent signal will assure a consistent release point and will avoid the possibility of release error due to variations that may occur in the non-electrical holding means described above.

Turning now to a detailed explanation of FIGS. 2D, 2E and 2F, FIG. 2D shows a mechanical latch in the position which locks thrust rod 15 to spindle 5, when the flyweights are in the most inward position. FIG. 2E shows the same latch in the final released position, when the flyweights are in the most outward position.

Two diametrically opposite pairs of rollers 21 roll on a flange 22 on spindle 5 and on two diametrically opposite lugs 23 on thrust rod 15. A pair of axles 24 fastened to a pair of cylinders 25 and 26 hold the rollers in axial alignment. These cylinders 25, 26 can turn freely on flange 22 and rod 15 but are held in axial alignment with each other by a set of keys 27. The keys allow slight axial movement between cylinders 25, 26; therefore, the thrust load is transmitted through rollers 21 without putting any significant load on the axles.

Release is triggered by moving a pair of prys, wedges or inclined planes 28 axially to the right, forcing rollers 21 in cylinder 26 to roll off lugs 23. The thrust load is then transmitted to plunger 16 (FIG. 2C) and rod 15 moves axially to the left. Wedges 28 project from a ring 29 through slots in flange 22. Ring 29 slides freely on spindle 5, but is forced to rotate with the spindle by the wedges 28 in the slots. The trigger moves a non-rotating collar 30 and the wedges axially.

One end of latch 18 is supported when rod 15 slides in a rotating member, which in this case is a hollow drive shaft 31, which turns rod 15 with keys or splines 42. Shaft 31 is supported by a bearing 32.

The direction of flywheel rotation would preferably be in the same direction in which cylinders 25 and 26 must rotate for release (i.e., clockwise in FIGS. 2D and 2E when viewed rightward from the left ends). Relatching can then be accomplished by momentarily retarding a cylinder with a brake 43 when starting, while the force from spring 20 exceeds the flywheel thrust and holds rod 15 against the right limit of its travel.

A trigger 70 comprises a yoke 44 which is pivoted on a pair of pins 45 in housing 2 and which contacts a pair of pins 46 on collar 30. A bias spring 47 attached to trigger 70 and housing 2 maintains the locked position until release is triggered manually or by an electrical solenoid 48, also attached to the trigger and to the housing.

FIG. 2E shows rollers 21 as if they revolved 90 degrees from their position in FIG. 2D, but the angle can be any value within a range set by the clearance between rollers 21 and ligs 23 and wedges 28.

Features of this latch are that there are no highly-loaded bearings and no radially outward mass transfers, which would reduce speed without producing any useful thrust.

The need for a hollow keyed drive shaft 31 can be eliminated by a latch designed to operate at the left side of FIG. 2C or by interchanging the positions of the motor and the injection device. The injection device must be designed for a pull, rather than a push, from the thrust rod in the latter case.

FIG. 2F shows a rotating hydraulic latch 18' in the locked position. A cylinder 33 at the end of spindle 5 is filled with hydraulic fluid F. An inner cylinder 34 contains fluid F which is at an elevated pressure in the locked position. Cylinder 34 has end walls with openings 35 through which fluid can flow freely. The pressure is produced by a piston 36 and rod 15, which transmits the thrust load to fluid F. Seals 37 and a seat 38 prevents leakage. Part numbers correspond to those in FIGS. 2D and 2E where corresponding parts are employed.

Inner cylinder 34 is moved a small distance to the right by collar 30 to form an opening at seat 38 and release the pressure on the left side of piston 36. The fluid flows between cylinders 33 and 34, and flows into the increasing volume to the right of piston 36 as the piston moves to the left. The fluid volume within the latch remains constant. No flow to or from the outside is required. A pair of seals 39 complete the sealing of latch 18' and are not exposed to high pressures. A projection 40 from inner cylinder 34, with a vent 41 to the atmosphere, permits a constant volume system and balancing of the trigger load.

The diameters of piston 36 and seat 38 can be proportioned to produce a particular trigger force at a particular speed in either direction. If the force on collar 30, originating with flyweights 8, is to the right in FIG. 2F, latch 18' will trip automatically at a load set by bias spring 47, a screw 49, and an adjusting knob 50 in the housing. Another feature of latch 18' is that it can easily be locked at any position of the flyweights and plunger 16 (FIG. 2C) before acceleration begins. This facilitates injection of varying serum volumes from one size cylinder or capsule.

Fluid pressures in the latch can be much more moderate than the injection pressures if the latch diameters are sufficiently large.

Figure 2G:
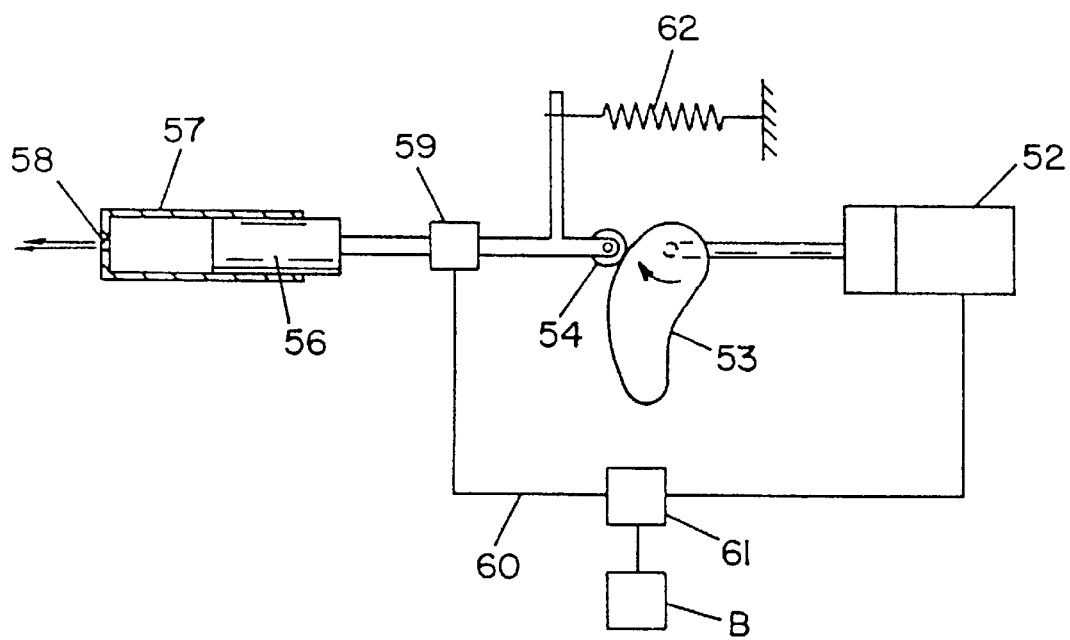
FIG. 2G is a schematic diagram of apparatus for the direct drive of the forces for an injection procedure.

In the direct drive system of FIG. 2G, a high torque gearmotor 52 rotates a cam 53 (clockwise in FIG. 2G) whose increasing radius directly drives a cam follower 54 which in turn transmits a drive force to compress a piston 56 in injection chamber 57 to expel the injectant through an exit port 58. A force transducer 59 continuously detects the force exerted on piston 56 and generates a feedback signal 60 that increases or decreases drive power to the motor drive through a controller 61 powered by a battery B, in order to maintain the target pressure throughout the injection cycle. A return spring 62 pulls piston 56 back to its starting position when cam 53 rotates beyond the maximum stroke of the injection cycle. An optional motor-generator and constant inertia flywheel (not shown) is also applicable for energy storage if insufficient short term power is available for a direct drive system.

The cam follower 54 and piston 56 in FIG. 2G could be replaced by other means for transmitting a drive force, and piston 56 and injection chamber 57 could have other forms rather than the piston and cylinder as shown. Piston 56 could be other ram means and the injection chamber could be other containers from which the injectant is expelled.

The above description is a general outline of the inoculation process with detailed reference to the means for developing injection pressure, system control, monitoring, motor drive and display apparatus of FIGS. 3 and 4. While it is our intent to provide safe, low cost and convenient-to-use hypodermic injectors, we also provide measures of electronic monitoring, motor drive and control not found in known jet injectors.

Figure 6:
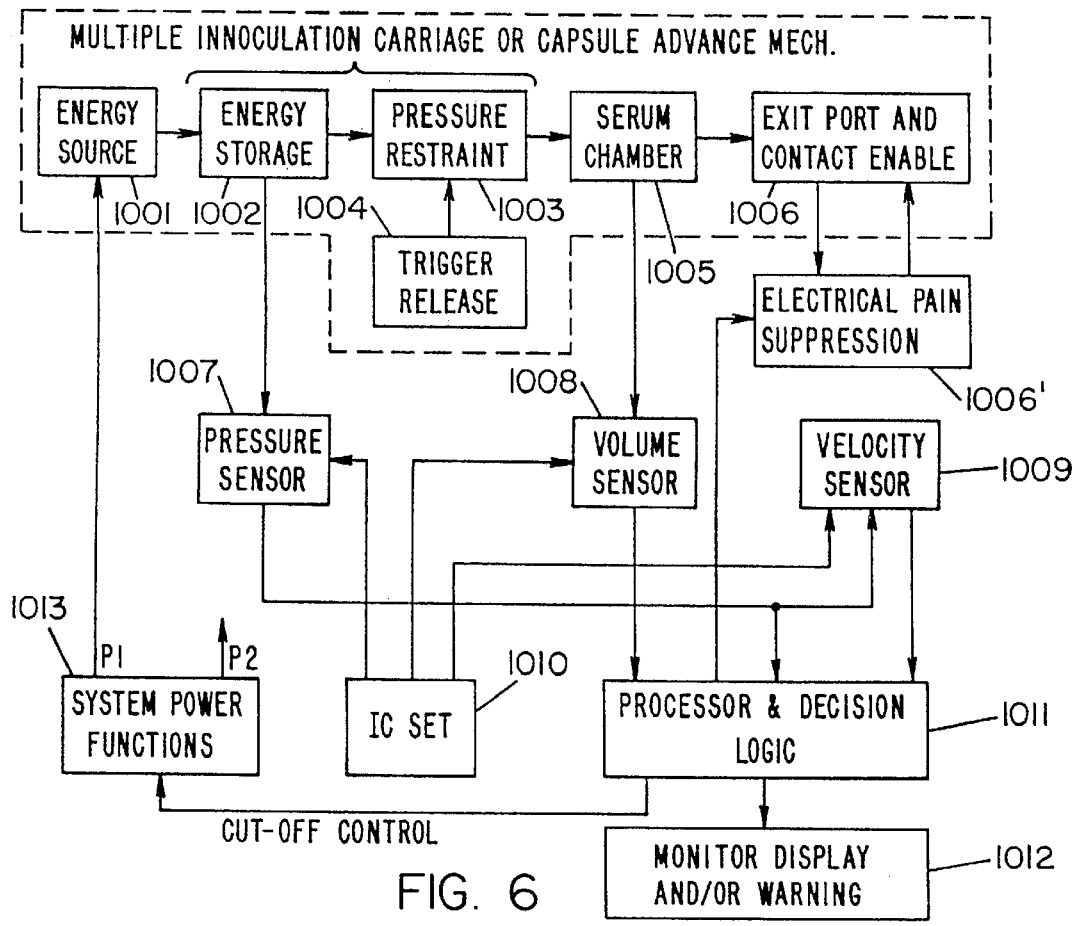
FIG. 6 is a block diagram overview of a multiple inoculation jet injector system in accordance with another embodiment of the invention.

FIG. 6 provides a block diagram functional overview of a hypodermic jet injector system in accordance with my invention. The dotted line of FIG. 6 provides a logical division between the mechanical portions of the injector system and the electronic monitoring, motor drive and control portions of the system.

The functional boxes 1001 through 1006 of FIG. 6 correspond to elements of the illustrative embodiment of FIGS. 2A and 2B as follows:

| FIG. 6 | FIG. 2A or 2C |
| --- | --- |
| Energy Source 1001 | Motor 221 |
| Mechanical Energy Storage 1002 | Spring 227 or flywheel 8 |
| Pressure Restraint 1003 | Detents 232 and 233 or latch 18 |
| Trigger Release 1004 | Not shown in drawing |
| Serum Chamber 1005 | Jet injector of FIG. 1 including Bellows 100 |
| Exit port and contact enable 1006 and electrical pain suppression 1006' | Output port 109 and guard ring 103 |

Although the illustrative embodiment of FIG. 2A employs an electrically-operated geared down motor 221 to compress the coil spring 227, this requirement can be fulfilled by a variety of manual arrangements utilizing gears or other means of mechanical advantage. While the spring is preferred for storing mechanical energy, the blocks 1001 and 1002 of FIG. 6 could be replaced by other arrangements, e.g., a powerful solenoid, gas, hydraulic pressure, the flywheel, or direct drive cam discussed earlier. The critical requirement of the blocks 1001 and 1002 is that the serum chamber 100 receives enough force for a sufficient period of time to assure an effective inoculation.

The monitoring functions of FIG. 6 inform an operator when the device is ready to perform an injection, i.e., all system parameters are within acceptable limits of performance. A warning is issued when performance is not within limits and the system is disabled in the event of a malfunction.

The pressure sensor 1007 of FIG. 6 monitors the status of the energy storage device 1002 and compares the magnitude of the stored energy to a target magnitude. When the magnitude of the energy stored reaches the target value, the storage of energy is terminated. The target value may be a default value established by the manufacturer or a value established by the operator on the basis of experience with different subjects, e.g., adults, children, animals, and/or types of serum. DNA technology, agricultural procedures and different types of senim may be better served with different pressures. The target pressure value is one of the "initial conditions" which an operator may set by controls in the IC Set function 1010 of FIG. 6.

The volume sensor 1008 provides assurance that a correct amount of liquid is used in each injection.

The velocity sensor 1009 of FIG. 6 determines the time required for the stored energy to decay to some predetermined value after an injection. The decay time is a measure of output port performance. If the output port is partially clogged, the pressure decays too slowly; and if the output port is worn or too large, the pressure decays too rapidly. If a failure is detected, a warning will be issued to the operator and the system is disabled until corrective action is taken.

The IC Set 1010 of FIG. 6 permits an operator to select initial condition values for the pressure sensor 1007, the volume sensor 1008 and the velocity sensor 1009.

The processor and decision logic 1011 issues control signals to the system power control 1013 and status signals to the monitor display and warning unit 1012.

In addition to the control and monitoring function described above herein, the circuit arrangements of FIG. 4 maintain a record of the number of injections completed or, in the case of the cartridge system described below in relation of FIGS. 7A and 7B, the number of cartridges remaining as the cartridges in the magazine are used up.

The implementation of the system functions by the arrangements of FIGS. 3 and 4 will be understood from the following description.

Digital inverters 310 and 312, resistors 314 and 316, and capacitor 318 are configured to form a reference frequency oscillator. The operating frequency $F_{r1}$ is determined by the time constant of the resistor 314 and the capacitor 318. This oscillator, or a separate oscillator, can provide the pain suppression signal for electrical pain suppression function 319 and surface contact pads or guard ring 321.

Digital inverters 300 and 302, capacitor 308, and variable sensing inductance 304 in FIG. 3 form a variable frequency reluctance transducer oscillator which has an operating frequency $F_P$. The operating frequency of the oscillator varies as a function of the value of the inductance in coil 304. The coil 304, which is not shown in FIG. 2A, is mounted at the center of recess 107 and inside the energy storage spring 227 and is partially covered by the reluctance shield 226 of FIG. 2A. It is noted that reluctance shield 226 is shown to the outside of spring 227 for illustrative clarity, however, it is ideally situated at the inside diameter of spring 227, which is quite large in order to develop 1700 psi or more as needed for an effective deep penetration injection for human use or 6000 psi or more and for sufficient penetration of a dairy cow. In any event, a change in the relative position of the coil 304 and the shield 226 as the spring 227 is compressed changes the inductance of the coil 304. Accordingly tile frequency of the oscillator, which is determined by the time constant of the inductance of coil 304 and the capacitor 308, is determined by the degree of compression of the spring 227. A reluctance transducer oscillator with a sensing inductance as described above is known from my U.S. patent application Ser. No. 07/625,942, filed Dec. 11, 1990, for "Inductance Systems." It is noted that other types of oscillator networks can also be used for these functions, for example, analog comparators or amplifiers.

Flip flop 320 is configured as a frequency mixer which provides a digital output signal which has a pulse rate $F_{d1}$ which is the difference between the reference pulse rate $F_{r1}$ and the oscillator frequency $F_P$. In the absence of pressure on the spring 227, the frequencies $F_{r1}$ and $F_P$ are equal and the pulse rate $F_{d1}$ at the "1" output of flip flop 320 is zero.

In the illustrative embodiment of FIG. 3, energy enhancement techniques drive motor 221 with a series of high speed, high energy and relatively high voltage pulses. The output of AND gate 338 controls the generation of the motor drive pulses. The inputs to the AND gate 338 comprise: the "0" output of the flip flop 336 which remains high until the target value of spring compression is reached; the BT conductor from pulse decoder 424; the "0" output of the flip flop 380, which is high except when the trigger is activated to initiate an injection; the output of the inverter 356, which is high until the charge on capacitor 348 reaches a critical value; and the output conductor of the reference oscillator. When enabled, the output signal of AND gate 338 turns the FET 340 on and off at the rate $F_{r1}$ of the reference oscillator. When the transistor 340 is on, current will flow from positive potential through inductance 342 and the transistor 340 to ground. When the transistor 340 is subsequently turned off, the energy stored in the magnetic field of coil 342 will discharge through the path which is comprised of diode 344 and capacitor 348. The resistors 350 and 352 are of relatively high value; therefore, very little energy is lost in the path to ground through those two resistors. The magnitude of tile voltage generated by the collapse of the magnetic field of coil 342 is very high and is dictated by the rate of collapse of the field. The rate of collapse is determined by the impedance of the discharge path. The diode 344 prevents reverse flow of current due to the buildup of voltage on the capacitor 348. Capacitor 346 is a stabilizing capacitor which provides an extra measure of current for the coil 342 during the ON state of transistor 340. When the charge and corresponding voltage on capacitor 348 reaches a predetermined value the output of the threshold detector 356 will go low and gate 338 is disabled. The predetermined value represents a charge and voltage large enough to advance the motor 221. When the output of detector 356 goes low, the output of inverter 358 goes high to enable transistor 360 to provide a path for discharging the capacitor 348 through the winding of motor 221. As the charge is depleted and the voltage on the capacitor falls below the threshold value of detector 356, the output of detector 356 goes high to enable gate 340 to initiate another cycle of charging capacitor 348; and the output of inverter 358 goes low to disable transistor 360. High speed charging cycles will continue until the flip flop 336 is set to the "1" state which indicates that the energy stored in spring 227 has reached the target value. In the drawing, the output labeled $Q_5$ is the "1" output of the flip flop 336 and the complement output is termed the "0" output herein.

Figure 3A:
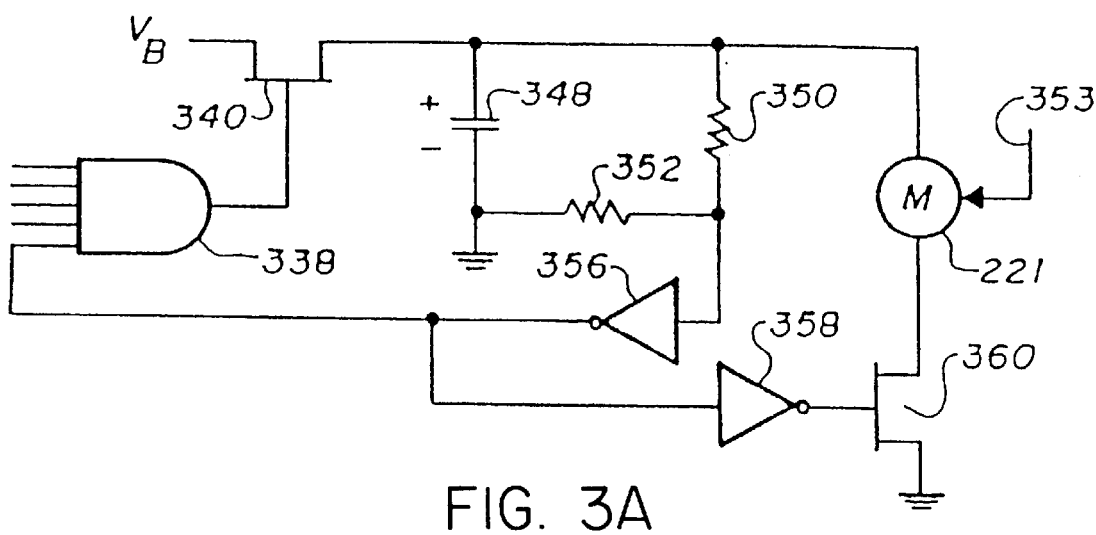
FIGS. 3A and 3B are schematic representations of alternative embodiments for the motor drive circuitry in the jet injector system of FIGS. 2 and 7.

The energy enhancement technique of the FIG. 3 embodiment allows for a power source that has neither the voltage or current capability for directly driving the motor. However, if the power source has a voltage level that satisfies that of the motor, but whose electrical current capability is insufficient, then the drive embodiment of FIG. 3A can be used. In this case, energy enhancement still applies, but the voltage amplification provided by coil 342 and diode 344 are eliminated and the corresponding loss in efficiency is eliminated as well. Instead, when all conditions for an injection are satisfied, gate 338 activates transistor 340 so that capacitor 348 is charged to the voltage level of the battery; that is, the mid-point of divider 350/352 is adjusted so that Schmitt trigger logic inverter 356 will change state when battery voltage is achieved on capacitor 348, and immediately thereafter, the motor is driven with closure of transistor 360 as described for the FIG. 3 embodiment. This scenario provides a high speed, high energy, albeit lower voltage, sequence of drive pulses to the motor. Capacitor 348 is selected to provide sufficient electrical current for a long enough time to exceed the design value for motor advancement.

Figure 3B:
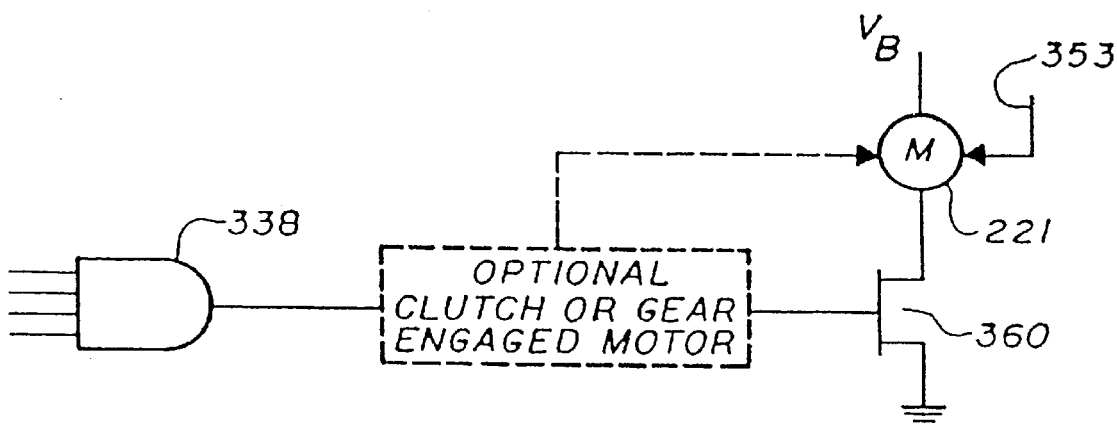

FIG. 3B shows an embodiment whose power source has enough instantaneous energy to drive the motor directly, i.e., one with enough current and voltage capability for driving the motor with no energy enhancement at all. In this case, transistor 340, coil 342, diode 344, capacitors 346 and 348, divider 350/352 and Schmitt inverters 356 and 358 are all eliminated. With this embodiment, the output of gate 338 will now drive transistor 360 so that the motor is connected directly to the power source when all conditions for an injection are met. A prototype of the "direct drive" system with a 9 volt alkaline battery achieved more than 400 injections in excess of 1700 psi each. With this arrangement, load time per injection is only 10 seconds; however, load time can be increased or decreased with variations in motor size, gear ratio, power capability and/or target pressure. It is also noted that for the same system, over 1,000 injections are achieved when using a higher energy density lithium battery.

While all of the jet systems described herein are smaller, lighter in weight and more convenient to use than those of the past, the selection of one drive technique as opposed to another is dictated by economics, acceptable load time and the primary use for the injector. For example, the FIG. 3 approach is the most compact because the total energy enhancement described will allow for a smaller motor/ battery combination, however, it is also the least efficient and will result in fewer "shots" for a given amount of initial energy. A good example for this system is its daily use by diabetics where load time is not so critical and where it is easily carried in a woman's purse or a gentleman's pocket. When the maximum number of injections is paramount, such as mass immunization by the military, veterinary, DNA or agricultural procedures, then a better choice is the other end of the spectrum as shown in FIG. 3B, that is, using a larger, direct drive motor, with lower voltage, higher efficiency and faster load time.

Finally, because of the wide adaptability of the inventive system, some applications might use motors with very high start-up current and/or free-wheeling rotors. If this is the case, the motor is ideally driven with an optional, electrically driven, clutch or gear engagement. In this way, the inertia achieved by the rotor at start-up is preserved by disengaging when capacitor 348 is charging, re-engaged when the next pulse of energy is given to the motor and will again disengage when completed. The entire sequence is conveniently controlled with the same signal that turns transistor 360 ON and OFF as capacitor 348 charges and discharges in the enhancement techniques of FIGS. 3 and 3A. When this is done, the signal to transistor 360 is synchronously delayed so that the mechanical linkage is optimally engaged at the same time that the energy stored in capacitor 348 is released into the motor. The feature can also be used with FIG. 3B, but its advantage is not as great because, in this case, once started, the motor stays on until target pressure is achieved.

Regardless of the method used for driving motor 221, flip flop 336 is controlled by the $A_N$ output conductor of counter 322, by an output signal of the digital window decoder 386, and by the BT conductor. The flip flop 336 is set to the "1" state when the $A_N$ output of the counter 322 goes high if the BT conductor is high; and is reset by the output conductor of the decoder 386. Counter 322, in turn, is controlled by the $F_{d1}$ signal at the output of flip flop 320 and by the output of flip flop 362. Flip flop 362 is set by a $F_{d1}$ signal at the output of flip flop 320 and reset by a $B_n$ output signal of counter 364. Counter 364 defines a period of time in terms of pulses of the reference frequency $F_{r1}$ and counter 322 counts the difference frequency pulses $F_{d1}$. Since counter 364 and counter 322 are reset at the same time by an output signal of flip flop 362, counter 364 provides a measurement window of time which runs from reset time to the next reset time. The $A_N$ output conductor will remain low until the deformation of the spring 227 reaches the target value. When the counter 322 reaches the $A_N$ count within the measurement time window, flip flop 336 is set and gate 338 is disabled. At the same time, the "1" output of flip 336 is transmitted to the warning function 388 to indicate that the device is ready for an injection procedure. Flip flop 336 can be set only if the "BT" input to the "D" terminal of that flip flop is high. As will be explained with respect to FIG. 4, the BT conductor will be high if the bellows test is satisfactory. The digital code which is stored in counter 322 during a measurement time interval corresponds to the instant deformation of the energy storage spring 227. The digital pulse decoder 324, in response to the digital code in counter 322, generates input signals for the BCD counters 326, 328. For example, if the deformation of the spring which is equivalent to one pound of force on the spring provides ten cycles of differential frequency $F_{d1}$, decoder 324 will convert the code in counter 322 to a single pulse for BCD counters 326, 328. With a count of one in the counters 326, 328, the BCD decoders 330, 332 provide signals to the display 334 to display the value, one pound. Any number can be displayed with appropriate decoding by pulse decoder 324. By virtue of the display 334, the operator knows that the appropriate level of energy is stored in the spring 227 and that an injection may be initiated. The flip flop 336 remains set until an injection has been successfully completed. If the velocity test fails, a warning in 388 will issue and flip flop 336 will not be reset. Accordingly, remedial action must be taken before preparation for another injection can be started.

The power on switch 375, in the lower left portion of FIG. 3, connects positive potential to the input of inverter 379 through the contact segments 370 and 371, detents 232 and 233, and line 377. The contact segments 370 and 371 lie in the recesses 108 on the back plate 104 shown in FIGS. 1 and 2. When the trigger is operated, the detents 232 and 233 are disconnected from the contact segments 370 and 371; and, because the input is referenced to ground through resistor 374, the output of inverter 379 goes high. A high signal from the output of inverter 379 increments a counter in 390 to display the number of injections completed from the current bellows; and causes the "D"-type flip flop 380 to be set to the "1" state. Consequently, the "0" output of flip flop 380 goes low which disables AND gate 338. The high signal on the "1" output of flip 380 enables AND gate 382 to pass $F_{d1}$ difference frequency signals to the input of counter 384. As explained earlier herein, the difference frequency will be reduced accordingly as spring 227 comes to some predetermined value after an injection. The count which is accumulated in the counter 384 is thus representative of the time required for the injection chamber to be partially collapsed. The window decoder 386 evaluates the count in the counter 384 on the basis of the expected values established by IC 2. If the count is larger than the expected limits, it is probable that the output port is plugged, and if the count is smaller than the expected limits, it is probable that the output port is enlarged beyond acceptable limits. In either event, a warning signal is displayed by the warning indicator 388 and the flip flop 336 will not be reset until remedial action is taken. If the count in counter 384 is within limits, an output signal of digital decoder 386 will reset flip flop 336 and the BCD counters 326 and 328. When that occurs, the cycle to drive the motor to load energy into the spring 227 will begin again. The time required for the chamber to partially collapse is short compared to the time required for the detents 232 and 233 to again settle in the recesses 108 and reconnect positive potential to the input of inverter 379. This time relationship is positively assured if a dashpot is employed to slow the return as suggested earlier herein. When the positive potential reappears at the input of inverter 379, capacitor 376 and resistor 378, which are configured as a high-pass filter, produce a reset pulse to flip flop 380 and counter 384 in preparation for the next injection. In the event that a very large volume injection is to be performed, the time required to inject the fluid may exceed the time for the detents 232 and 233 to settle in recess 108. In that case the illustrative high-pass reset circuitry can be replaced with circuitry with appropriate delay.

FIG. 4 provides an arrangement for testing the integrity of the liquid-filled bellows 404 or any other type of fluid-filled cartridge. Inverters 400 and 402 are configured as an oscillator in which the output frequency $F_b$ is determined by the impedance across the entire bellows 404. Inverters 410 and 412 are configured as a fixed frequency oscillator having a frequency $F_{r2}$; and flip flop 420 is connected as a frequency mixer for the signals $F_{r2}$ and $F_b$. In the configuration of FIG. 4, the collapsing bellows behaves as a variable resistance; therefore, the frequency of the mixer output signal $F_{d2}$ is minimum when the bellows is full. As the bellows collapses, the impedance decreases and the differential signal $F_{d2}$ increases. The counter 422 accumulates the $Fd_2$ signals during a measurement time interval defined by the "0" output conductor of flip flop 362 of FIG. 3, and pulse decoder and display 424 displays bellows status information. The use of the time period provided by the $D_N$ count is for purposes of illustration. In the event that a different time period is desired, additional counter outputs and flip flops are provided. The arrangements of 424 evaluate the interval count in counter 422 on the basis of the IC set 3 information which defines a range or window of acceptable values. If the count falls within the range of acceptable values, a high BT signal will be generated and flip flop is set on occurrence of the next succeeding $A_N$ signal from counter 322. However, if the serum within the bellows has excessive voids, clots or an incorrect consistency for some other reason, the $F_b$ frequency will fall outside the acceptable range and the count in 422 will fall outside the preselected window of performance.

It should be noted that fluid may be used as a dielectric material in an alternative embodiment in which a variable capacitance determines the frequency $F_b$. In that embodiment the variable bellows is located at the position of the capacitor 408 and a fixed resistor placed at the position 404 in FIG. 4. In this case, the two ends of the bellows form the capacitor plates and the serum fluid is the dielectric material. As the length of the bellows decreases, the capacitance increases and the frequency $F_b$ decreases.

Figure 5A:
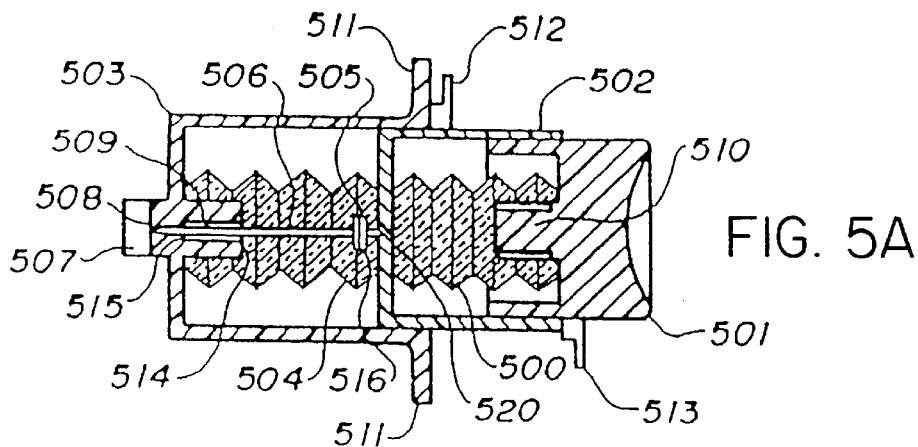
FIGS. 5A through 5E illustrate side, cross-sectional views of a needle hypodermic injector in accordance with another embodiment of the invention.

FIGS. 5A to 5D show a needle-type hypodermic injector in accordance with my invention in various stages in the use of the injector. The injector of FIG. 5A comprises a bellows 500 sealed with end cap and ram 510; a front housing 503; a rear housing 502; a pressure piston 501; a needle output port 508 with a flange 511; a bellows-shaped needle sheath 504; and a removable cap 507. FIG. 5A illustrates a fresh injector prior to use. As in the injector embodiment of FIGS. 1 and 2, the support guide rings 116 of those figures may be employed in the embodiment of FIGS. 5A to 5D. The bellows 500 may contain a liquid serum or a lyophilized (freeze dried) vaccine. In the latter case, a liquid which is stored in the sheath bellows 504 is driven into the bellows 500 as described below herein. The bellows 500, the rear housing 502 and the front housing 503 all may be fabricated of clear plastic material so that the operator can observe whether or not blood is drawn into the bellows 500 when the pressure piston is slightly withdrawn.

Figure 5E:
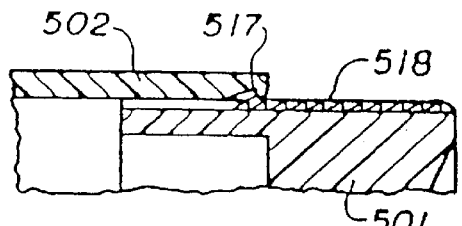
Figure 5B:
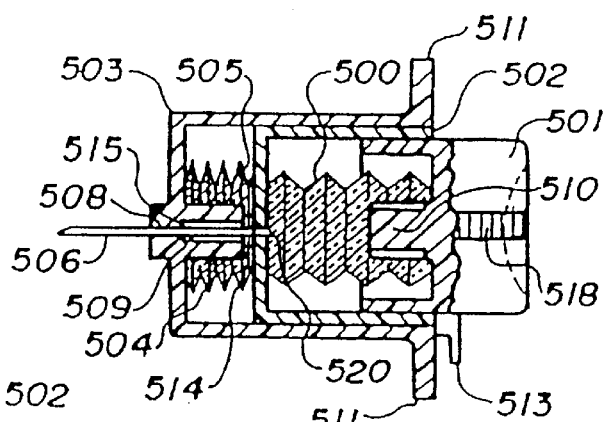

The breakaway seal 512 and the cap 507 are removed to permit the operator to depress housing 502. The need to remove the cap 507 may be eliminated if the cap 507 is made of a self-sealing material, e.g., pure latex rubber. Typically, the thumb is placed on the pressure piston 501 and index finger and the adjacent finger are placed on the flange 511. The resistance of the sheath bellows 504 is sufficient to cause the bellows to expand after use; however, the resistance of the bellows 504 is small compared to the force required to compress the liquid bellows 500 to eject the liquid through the needle output port. Therefore, as pressure is applied between the flange 511 and the pressure piston 501, the sheath bellows will begin to collapse and needle exposure will begin. As the sheath bellows is collapsed, the right-hand side 520 of needle 506 will puncture the membrane separating sheath bellows 504 and serum bellows 500. As compression continues, the liquid residing in sheath bellows 504 is forced into serum bellows 500 to form the fluid state of the desired serum. Ultimately, needle flange 505 will engage the surface 514 therein, after removal of breakaway seal 513. Continued pressure will force the serum in 500 to be expelled through the exit port of needle 506, said serum being unable to re-enter 504 because it has collapsed to zero internal volume. A foam ring 516 positioned on the right side of flange 505 serves as a cushion to prevent flange 505 from opening the membrane to a greater extent than that of puncture point 520. The membrane in 500 also can be made of self-sealing latex diaphragm material which will tend to hold the needle in place after the injection is completed and the sheath is again extended to cover the needle. The first intermediate state of the injector is illustrated in FIG. 5B.

In cases where the serum is stored in bellows 500 in a liquid state, the bellows 504 can be replaced with a simple coil spring. However, if as suggested earlier herein, the vaccine is stored in the lyophilized state, the fluid required to turn the vaccine to the liquid state is stored in the bellows 504. In this latter case, the liquid in bellows 504 is forced into bellows 500 through a hole in the membrane of the bellows 500 which is breached when the bellows 504 is first compressed to begin exposure of needle 506.

Figure 5C:
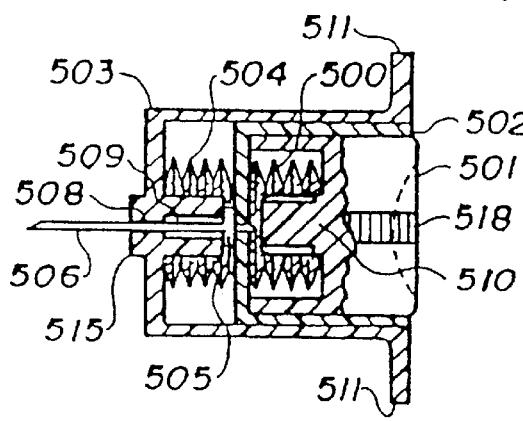

After the needle is inserted into the injection site, the breakaway seal 513 is removed and pressure is applied between the pressure piston 501 and the flange 511 to collapse the liquid bellows 500 and eject fluid through the output ports into the injection site. The state of the injector after depletion of the injection fluid is illustrated in FIG. 5C. As shown in FIG. 5E, a sawtooth pattern 518 on the outer surface of the pressure piston 501 and a single sawtooth 517 on the inner surface of the rear housing 502 permit the pressure piston 501 to be advanced into the member 502 and thus compress the bellows 500. However, the cooperation of 517 and 518 prohibits withdrawal of the piston 501 after engagement of 517 and 518. As an option, the end of the ram 510 is shaped to strike and crush the end 520 of the needle 506 when the bellows 500 is fully collapsed. This will further assure that the needle injector cannot be reused and will tend to retain the needle in engagement with the bellows 500 when the sheath bellows 504 and the sheath 503 are extended to cover the needle.

Figure 5D:
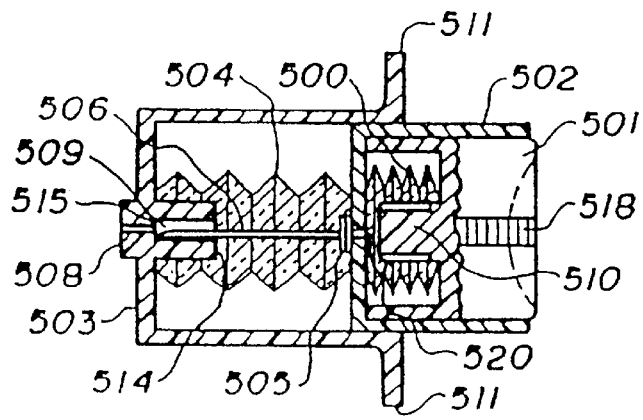

After the needle is removed from tile subject and pressure between 501 and 511 is removed, the bellows 504 expands as shown in FIG. 5D. As is seen in FIG. 5D, when the needle sheath bellows 504 extends to its full length, the needle 506 is withdrawn from the needle guide 508. This occurs because, in preparation for the injection, end 520 of needle 506 penetrated the membrane to breach the serum chamber. Because the needle guide opening 508 is small compared to the trap opening 509, it is difficult if not impossible to again collapse the bellows 504 without the end of the needle 506 hitting the end wall 515 of the trap section 509. The tendency of the needle to hit the wall 515 can be enhanced by imparting a small bend in the needle 506 prior to initial installation into the guide opening 508.

The above discussion for FIGS. 5A to 5D deals with the various steps for a special case insertion of a hypodermic needle into an injection site. Capsules 5A to 5D and needle 506 can also provide several other valuable functions. First, if the housing is designed to fit into a jet injection chamber similar in nature to that of FIG. 7, needle 506 issues the highly desirable dispersion pattern of a jet injection stream much deeper into the body. This capability provides superior medical treatment in some cases. Second, if needle 506 is shortened to exit the capsule to the appropriate length, it will deliver lyophilized medications while deriving all of the advantages of a perforator jet injection. Third, if needle 506 is made even shorter by the correct amount, it will not exit the housing at all, but instead, the capsules 5A to 5D will serve as a non-penetrating, flat, prior art orifice, similar to that shown in FIG. 9D but capable of delivering a lyophilized jet injection to humans or thinner-skinned animals.

Figure 7:
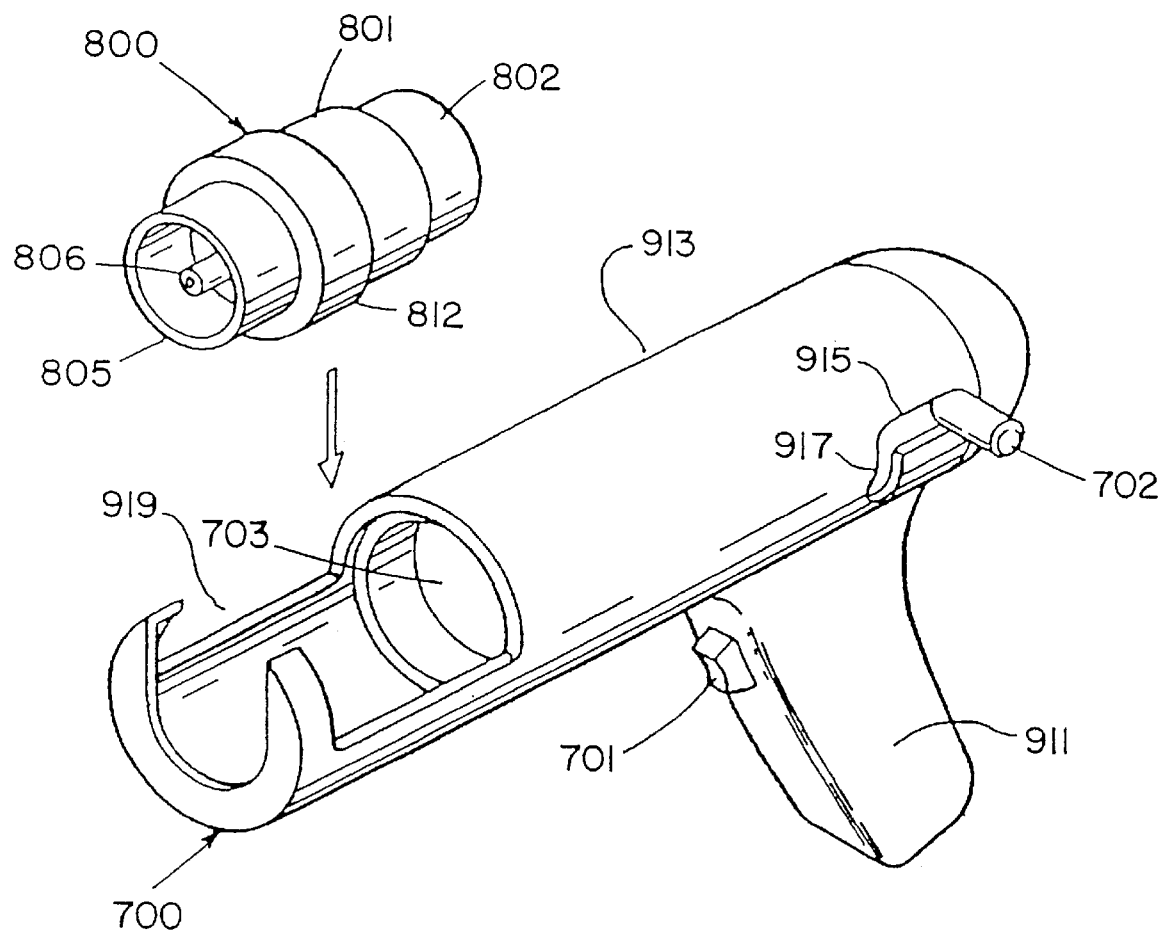
FIG. 7 is a pictorial view of another embodiment of a jet injector in accordance with my invention.

FIG. 7 shows an alternative embodiment of a jet injector system in which the serum for each and every injection is individually contained in its own collapsible cartridge. A dispenser 700 includes a handle 911 from the forward end of which extends a trigger 701. A muzzle 913 includes at its rearward section a lever 702 extending laterally through a longitudinal slot 915 in muzzle 913 which terminates at its forward end in a downward extending portion 917. Dispenser 700 includes at its forward end a receptacle or opening 919 for receiving a cartridge 800 holding a serum for injection into a recipient. Dispenser 700 includes a piston or ram 703 for acting on cartridge 800 to effect an injection. Cartridge 800 is described below and shown in FIGS. 8A and 8B.

For illustrative purposes, tile cartridge 800 shown in FIG. 7 is grossly oversized, wherein a normal injection requires from ½ to 1 cc of serum (from about 0.031 to 0.061 in$^3$) and the actual cartridge size is commensurate with that volume. Since the system of FIG. 7 can be proportioned to handle single-shot or multiple-shot cartridges, the smaller size is also true for the magazine embodiment of FIGS. 7A and 7B, that is, the illustrative magazine is many times larger than that needed for the N cartridges shown in the figures. For a single-shot arrangement, the lever 702 is drawn to the rear to permit removal of a used cartridge from receptacle 919 and a fresh cartridge installed. After a fresh cartridge is installed, the lever 702 is moved forward, to the left in FIG. 7.

Figure 7A:
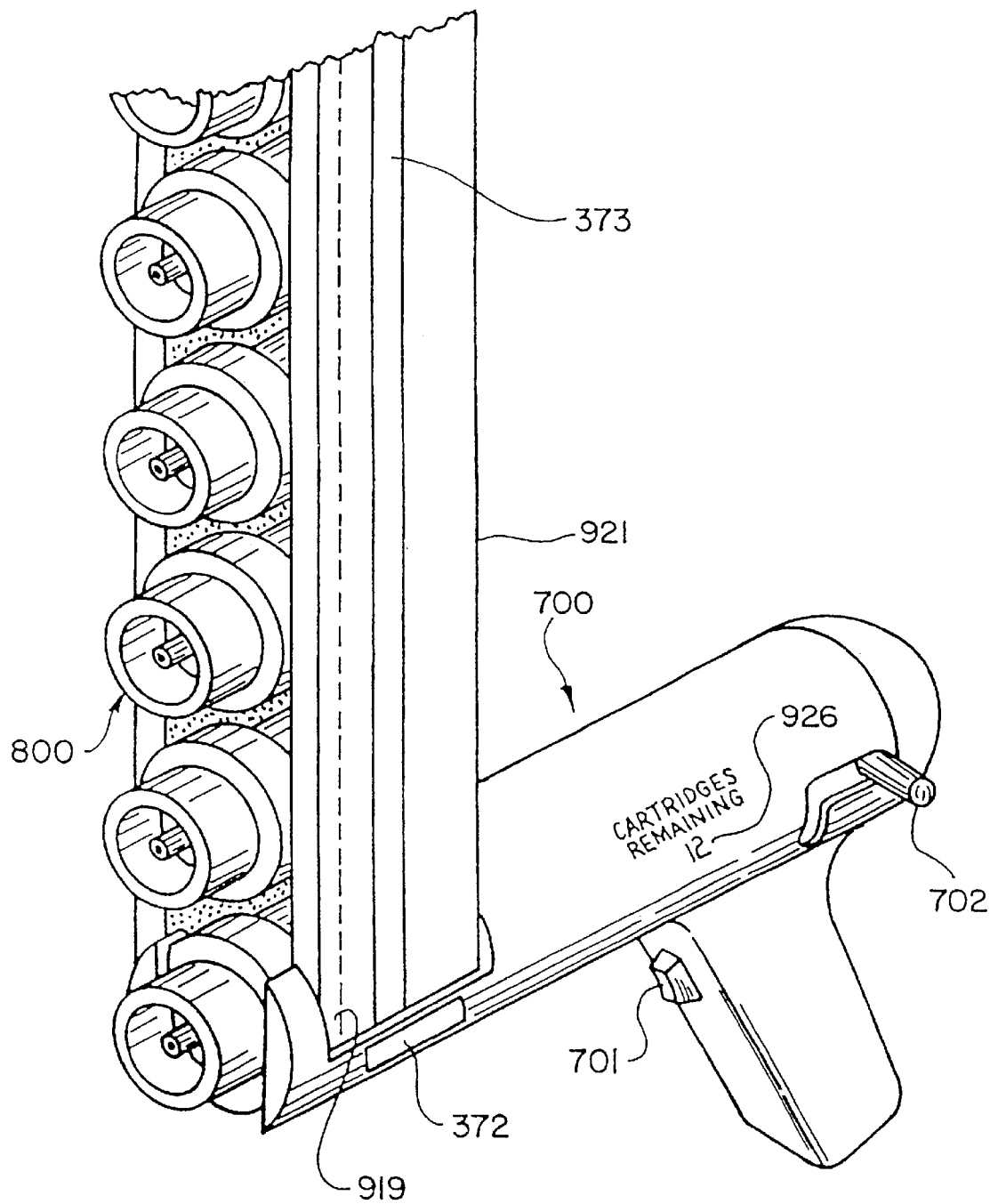
FIG. 7A shows an oversized perspective view of the injector shown in FIG. 7, with a fresh magazine with N unused injections positioned in the dispenser.
Figure 7B:
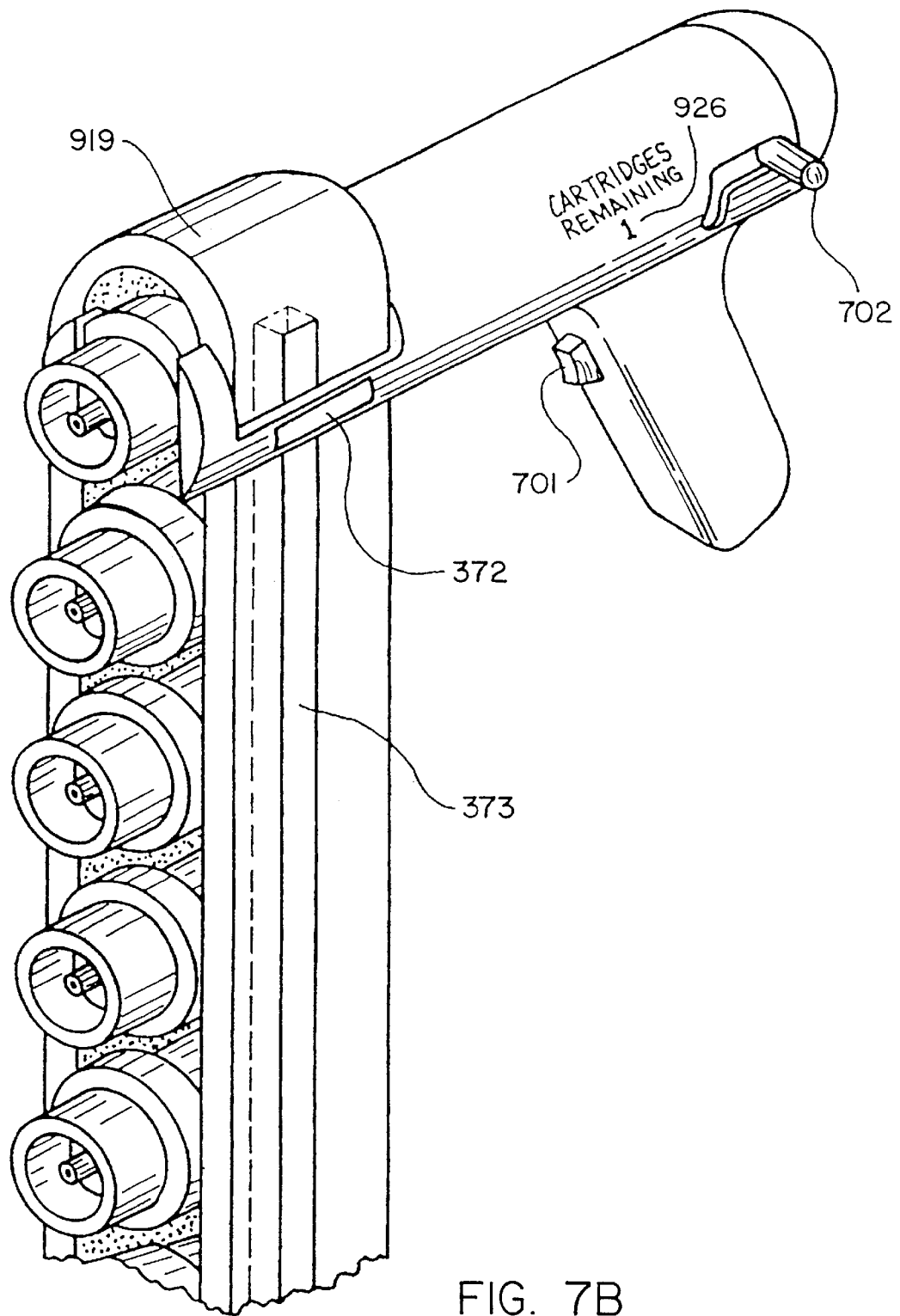
FIG. 7B shows the oversized magazine illustrated in FIG. 7A with the injections having been used.
Figure 7C:
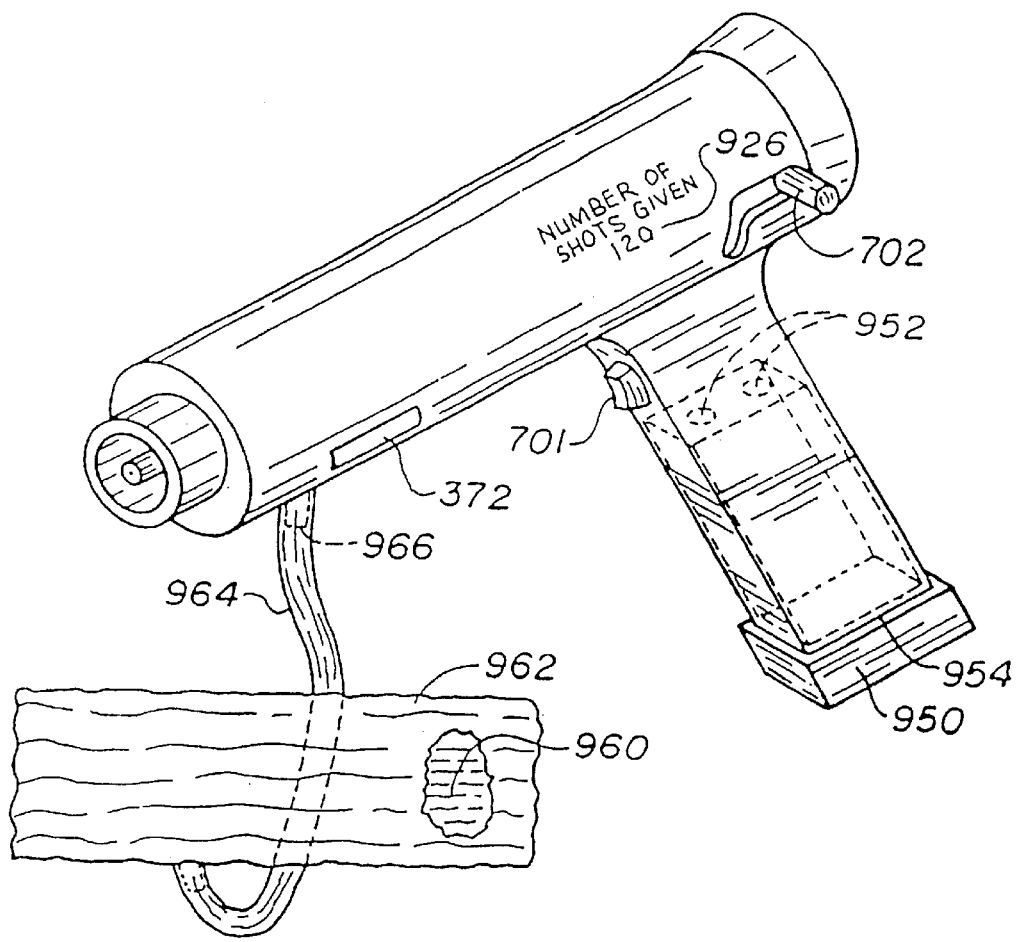
FIG. 7C is a pictorial view of the jet injector wherein the rechargeable power source is a removable module and a multi-dose container is connected to the injection head to permit the rapid continuation of an injection procedure for a large number of subjects.
Figure 7C:
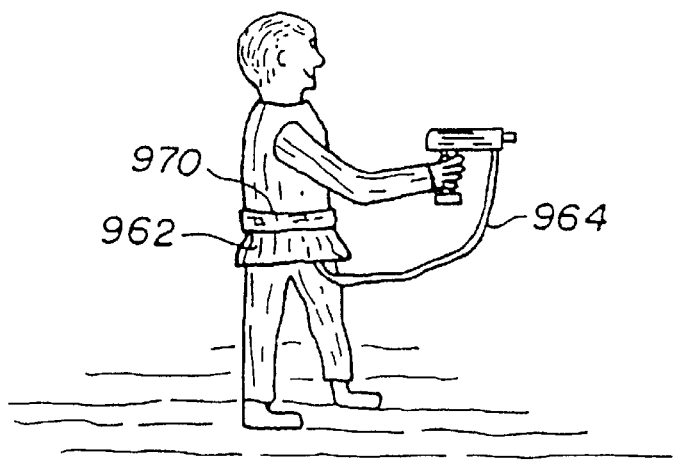
Figure 7D:
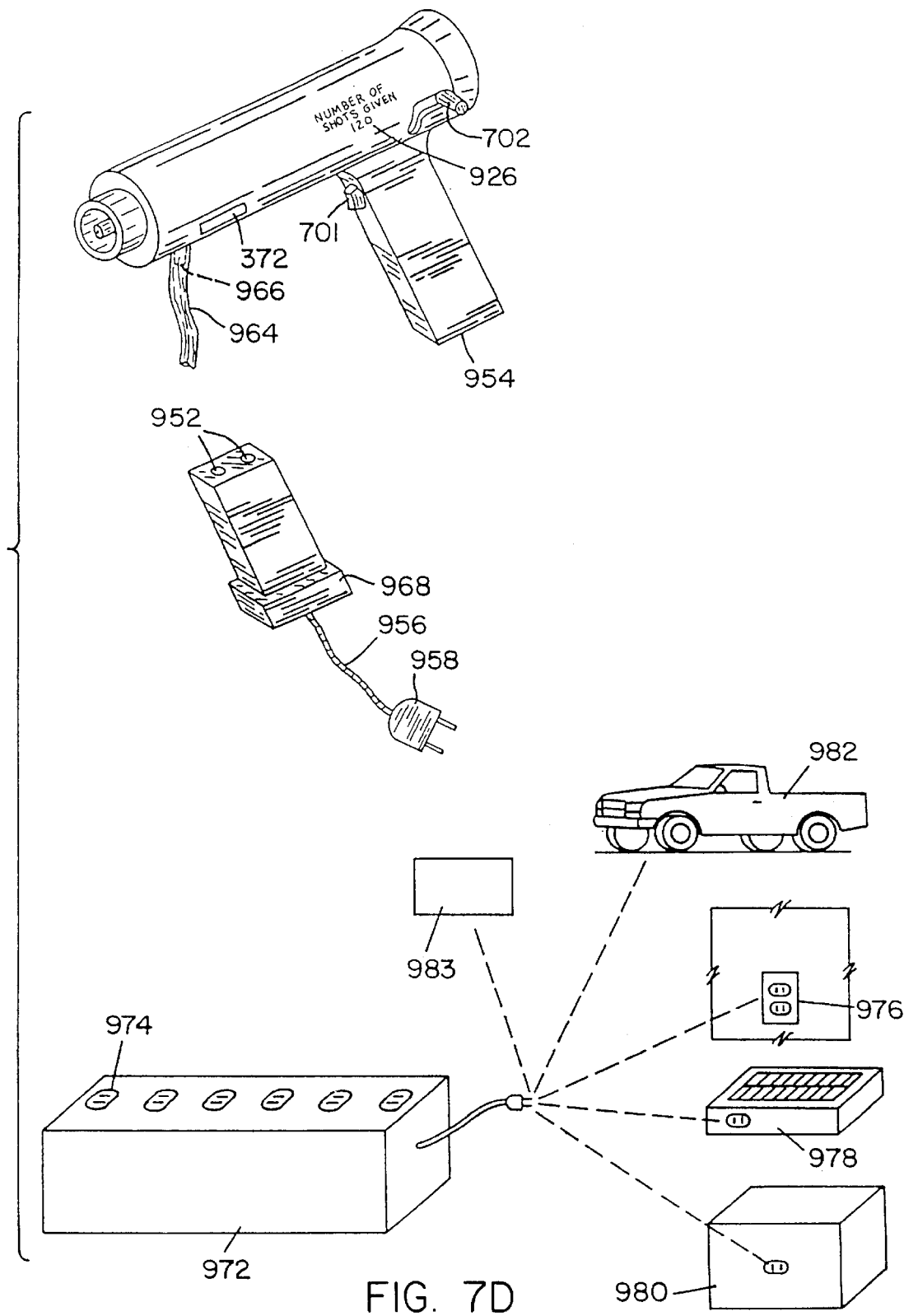
FIG. 7D shows the format of another embodiment of the invention showing an injector capable of being driven by alternate sources of electrical power.

With regard to the magazine embodiment of FIGS. 7A and 7B in which the N cartridges 800 are serially introduced into system 700, which is shown identical to that in FIG. 7, many magazine configurations are possible for sequential loading into and out of the injection chamber. For example, much in the manner of a modern pistol with a linear magazine containing N bullets or, the revolver-type weapon in which the bullets rotate into the chamber or, as shown in the oversized preferred embodiment of FIGS. 7A and 7B, there is shown the entire magazine 921 which is simply detented through opening 919 in the injector chamber as each new injection occurs. In this latter arrangement, the cartridges are not extracted at the completion of each injection, but simply remain in magazine 921. This feature is especially important for the prevention of unsafe littering at the scene of mass immunization programs such as the military or activities of the World Health Organization in their worldwide efforts with disease control. Other methods of collection and storing the used cartridges are also possible, for example, a magazine that has an evacuated volume equal to that of the loaded cartridges, and into which the used cartridges will drop at the conclusion of an injection.

A manual advance for the magazine can be implemented with lever 702 or an automatic advance is realized with a spring configured ratchet assembly that is "wound up" when magazine 921 is slipped into the bottom opening of the dispenser 700 and urged upward until latched into the initial position for the injection sequence. Since the system is electrical in nature, a motor advance is the most convenient of all; however, power conservation for a multitude of high pressure injections has a higher priority in many applications. As discussed earlier, any suitable driving force can be utilized to drive pressure piston 703 forward to collapse the serum chamber 804 in cartridge 800 (as explained below) when said cartridge appears at the injection site.

Switch 375 is basically the ON-OFF switch for system power. The manner in which the power is provided can be carried out in a number of ways, wherein the one or more ways selected is normally dictated by the application and/or user preference. Several embodiments are described below.

Referring to FIG. 3 for one such way, switch 375 is simply turned ON, after which flip flop 336 automatically enables gate 338 and turns ON motor 221; when target pressure is detected, flip flop 336 disables gate 338. This cycle continues until a system failure occurs or the injection capability is depleted. In a single or multiple cartridge system, the detent action of contacts 232, 233 is provided as part of the trigger mechanism 701 in FIGS. 7, 7A and 7B.

Figure 3C:
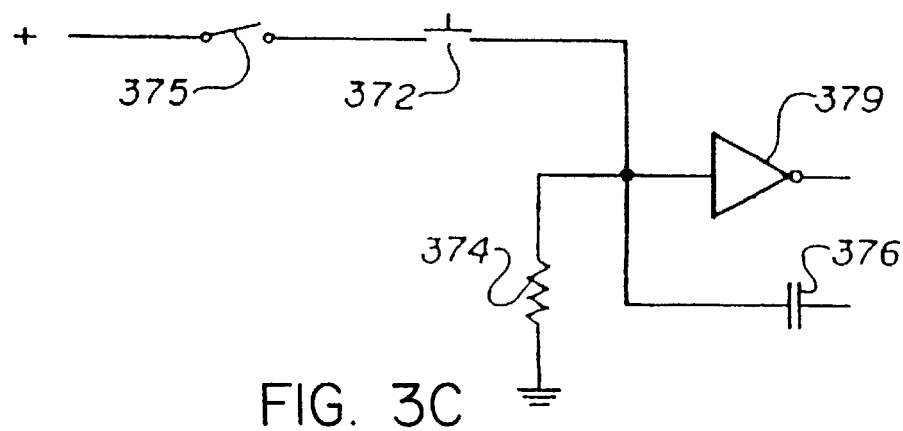
FIG. 3C is an alternate embodiment of the power switch shown in FIG. 3.

Turning to FIGS. 7A and 7B for another embodiment, momentary switch 372 in FIG. 3C replaces the latching contacts 232, 233. Switch 372 could be temperature sensitive and would only be enabled if a temperature threshold is reached. Moreover, switch 372 also can only be enabled if an access code is entered, as for example by an access key. Switch 375 still provides primary power to the system, but switch location 372 will remain open until all of the following requirements are met: (1) the magazine is securely positioned in the dispenser, after which switch 372 closes as it engages the first cartridge through slot 373 in the wall of magazine 921, (2) switch location 372 is enabled when the user applies pressure to guard ring 103 or 805 when the ring is brought into firm contact with the injection site, (3) the temperature threshold is met, and (4) the access code is entered. These features provide additional levels of safety by preventing accidental firing of the injector until the user is ready and/or prevents use by illicit drug users or other unauthorized people. In the case of temperature, damage is prevented to the injector or user when the injectant, whose viscosity is temperature-dependent, is too thick to allow for a safe and timely passage through the small diameter orifice under the influence of very high pressure. Other embodiments of switch location 372 are also possible and will depend on the level of safety required for a particular application.

A MANUAL/AUTO select is provided in another embodiment, wherein the manual mode switch location 372 is actuated by the user rather than by the cartridge, the guard ring or temperature detector in the AUTO mode. However, the AUTO mode is also provided, as described in the preceding paragraph.

When the magazine and cartridge embodiment is used, counter and display function 390 will electronically measure and display the number (shown as 926 in FIGS. 7A and 7B) of "live" cartridges actually found in the magazine. The counter and display number will then proceed with a countdown to zero as the cartridges are used. Again, this feature is important for situations where a magazine is removed and then returned to the dispenser for a later round of injections.

It is clear that in the magazine-type system, the expended cartridges can be safely disposed of; however, for purposes of economy in certain situations, the magazine can be ruggedly built for multiple long term use, in which case the entire magazine can be returned to a center for disease control, sterilized and reused in whole or in part. In one such embodiment, the cartridges themselves are reusable, but the exit nozzle is removed and replaced in the same manner as described for the multiple-dose cartridge of FIGS. 1 and 2. If the magazine is reusable, a preferred embodiment of this feature has the cartridge counter, its processor, display and a power source ideally located right in the magazine. With this embodiment, no count initialization is necessary because it simply detects the live cartridges found in the magazine on a real time basis whether the magazine is in the dispenser or not. In fact, this technique is useful for other magazine-oriented applications such as pistols, shotguns, rifles and automatic or semiautomatic weapons of any type. For such a system, a low battery warning would be used with the independent counter system as well. A specially designed version of the reluctance transducer and processor described for FIG. 3 is ideally suited for this embodiment.

Finally, as pointed out earlier, it is noted that a dispenser similar to that of FIG. 7 can be used for the needle oriented cartridge of FIGS. 5A–5E. Further, if the FIGS. 5A–5E cartridge is designed into the magazine structure of the FIG. 7A dispenser, then N needle-type cartridges can be administered in much the same way as the jet injector embodiment, but with greater efficiency and speed than that of the individual cartridges, while still providing the highly desirable dispersion pattern of a jet stream, and with even less risk to the population because the entire magazine remains under the watchful eye of the immunization team. As in the case of the FIG. 5 embodiment, the jet injector of FIGS. 7, 7A, 7B, 7C, 7CC, 7D, 7E, 8A and 8B can be fabricated of clear plastic material so that the operator can observe if the needle has penetrated a blood vessel after insertion, but prior to expelling the fluid. This is possible by virtue of an automatic micro-withdrawal of the pressure piston under the influence of the monitoring and control sequence of the electrically driven system.

FIGS. 7C, 7CC and 7D offer alternatives to FIGS. 7A and 7B by allowing for a rechargeable power source and an even larger multi-shot system. Typical applications are veterinary and agricultural uses where the multiple-shot cartridge system is replaced by serum container 962, or for use at remote locations where grid power is not available.

Viewing FIG. 7C, the correct dose of serum 960 is pulled out of container 962 through connecting tube 965 and into the injection head through access nipple 966. This will occur each time the ram is pulled back in preparation for the next shot, wherein every dose is administered through the same orifice 969. For veterinary use in particular, the periodic (sometimes daily) administration of the BST hormone to a herd of dairy cows becomes a very efficient procedure. With this scenario, serum container 962 is pre-loaded with the correct number of doses and is then carried by the user on waist or shoulder harness 970 as shown in FIG. 7CC, and the entire herd can be quickly inoculated. Also shown in FIG. 7CC is an additional fluid container 963 with a dye material that is transported to exit nozzle 967 through connecting tube 964. Especially useful for the injection of large animals in close proximity to each other, an appropriate amount of dye is drawn into the dye chamber at the same time serum is drawn into its chamber. The dye is expelled and deposited at the injection site as an indicator to show which of the animals has been injected with a particular material. This feature will prevent the adverse effects no injection at all or having an animal receive the same material more than once.

In FIG. 7C, power pack 950 is inserted and removed from access port 954 of the jet injector housing, wherein electrical contact 952 connects power to the injector. With this approach, the number of shots available from each source is not quite so critical, whereas it would be inconvenient for members of an immunization team, health care, agricultural or veterinary workers to repeatedly change and dispose of the battery. All they have to do is carry a number of sources in a storage harness, change them as each is depleted, and then have the entire group recharged with solar energy for isolated areas or a standard AC or DC source at more convenient locations.

Finally, power adapter 968 in FIG. 7D can be inserted into the injector housing in place of power pack 950 to allow for operation from other power sources if the portability of small battery operation is not required. For example, adapter 968 can be connected directly to an adequate source of external power or to power pack 972, wherein the injector is then powered with a non-disposable source of external energy that is transported to the remote location along with the injector, the medications and the health worker units. External source 972 can be a high capacity rechargeable battery or a storage capacitor whose value is large enough to supply N shots before recharge is needed. Recharge of power pack 972 can come from grid power at socket 976 (if available), or as an alternative, a solar panel trickle charger 978, a portable generator 980 or directly from a vehicle's power system 982 if such vehicle is available to the health care workers. In some remote locations, powerful solar systems 983 located nearby or on the roof of the health care facility are also conveniently used.

Figure 7E:
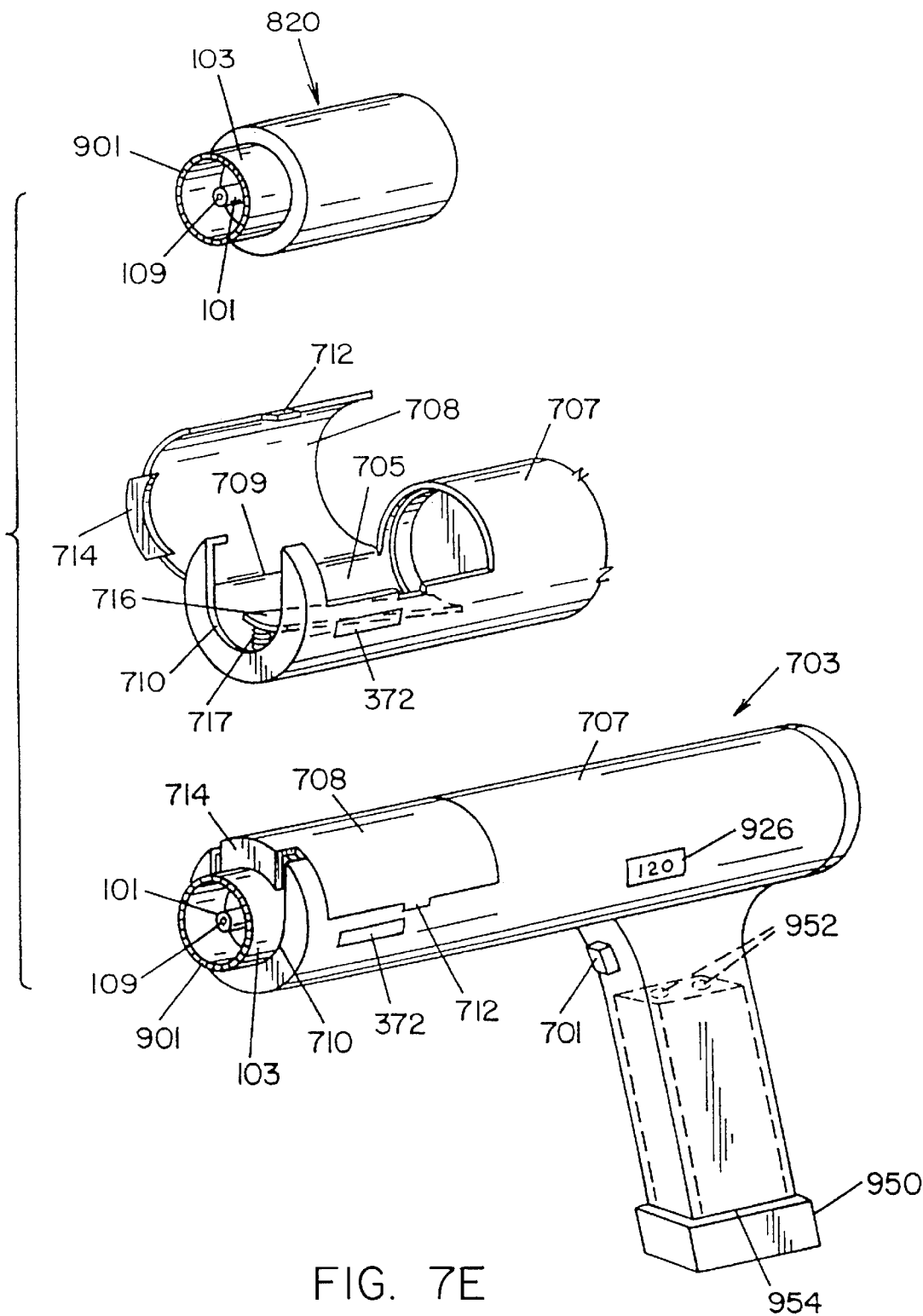
FIG. 7E is an exploded pictorial view of a jet injector system according to another embodiment of the invention, using thin-walled capsules in a high pressure injection chamber.

An injector system 703 of FIG. 7E illustrates a form-fitted, barrel-like restraining chamber 705 defined by a cylinderical barrel 707 forming part of the barrel and mounted on a hinge 709 and a cooperating door 708 which together provide the support needed for a high pressure injection with an inexpensive, thin-walled capsule 820. Capsule 820 can have a wall thickness of from 0.01 inch to 0.05 inch. These capsules 820 are discarded after each injection in the same manner as the disposable needle and syringe, except that the inconvenience, danger and cost of disposal for needle injections are eliminated. To load a capsule, door 708 is opened and capsule 820 inserted into restraining chamber 705. An access groove 710 accommodates and supports the guard ring end 103 of capsule 820. This end of capsule 820 also has a non-slip surface 901 as well as exit orifice 109. After capsule 820 is inserted, door 708 is secured in the closed position with a latch 712. The form-fitting chamber 705, a lip 714 on door 708 and groove 710 work together to hold capsule 820 securely in place to prevent any damage during the high pressure injection. A spring loaded arm 716 having a spring 717 attached to the interior of barrel 707 is compressed when the capsule is inserted and ejects the capsule when door 708 is opened; thus, physical contact and the risk of cross-infection for the health worker is further reduced when the injection is completed. Other parts of the injection system similar to those of the apparatus of FIG. 7D are given the same reference numerals.

Figure 7F:
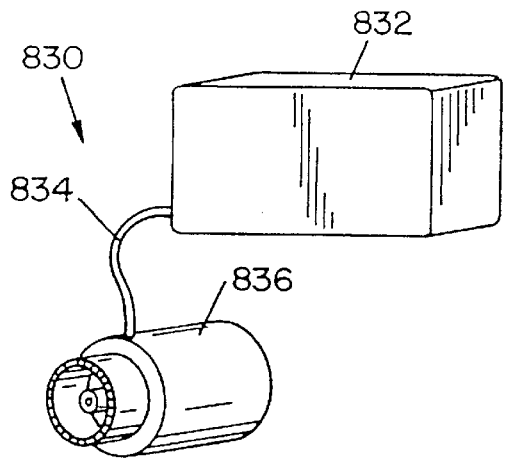
FIG. 7F is a pictorial view of a disposable, anti-gumming sub-system according to another embodiment of the invention, having a replaceable serum container, connecting hose, injection chamber and exit orifice as a single unit.

The FIG. 7F embodiment has good utility with large scale injection programs for animals and is an alternative to tile replaceable capsule. Subsystem 830 is a low cost combination comprising serum sack or chamber 832, connecting passageway or tube 834 and thin-walled injection capsule 836 all supplied as a single unit. When a particular medication is given to a herd of cattle, serum sack 832 is filled with the selected medication and inexpensive capsule 836 is inserted into the highly restrained injection chamber 705 of injection system 703. When the injection procedure is completed, the entire subsystem 830 is removed and stored for future use or discarded. This system will avoid the problem of gumming-tip the injector for situations and/or locations that make it inconvenient to clean the device in a timely manner as, for example, for large numbers of feed cattle on the range or when they just come in for treatment.

Figure 7G:
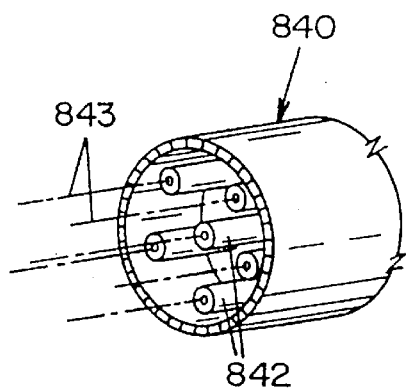
FIG. 7G is a pictorial, partial view showing a multitude of exit orifices from a single injection chamber.
Figure 7G:
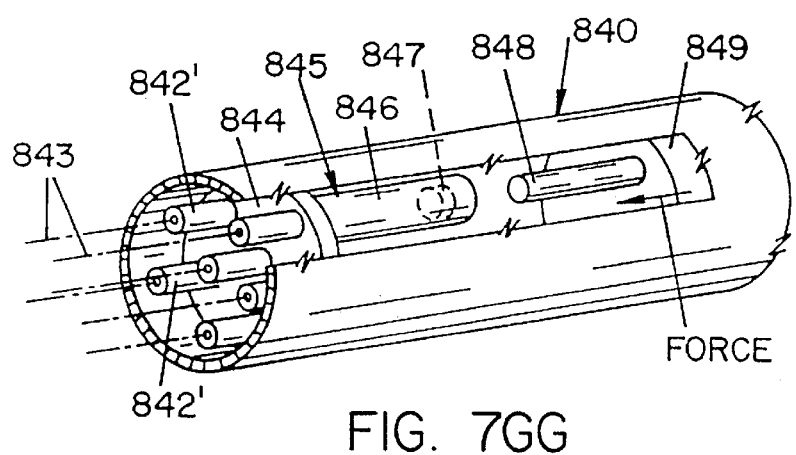
Figure 7G:
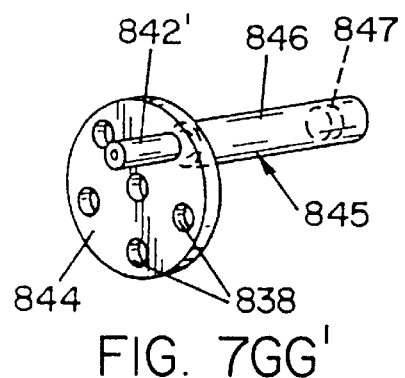

FIGS. 7G and 7GG show a capsule or injection barrel 840 intended to illustrate two different embodiments of an injection head with multiple exit ports. In the first case shown in FIG. 7G, a set of multiple exit ports 842 provide a number N jet stream of a fluid 843 from a single serum chamber. This technique has utility for advantageously reducing injection time for very large doses, sometimes in excess of 5 cc for large animals such as cows. With small exit ports on the order of 0.004 to 0.012 inch as required for a high velocity, piercing jet stream, the amount of time needed to discharge the fluid with a single port is quite long, up to three seconds, giving the animal ample opportunity to move before the injection is completed. This first embodiment is intended to avoid that problem.

The second embodiment is shown in cut-away form in FIG. 7GG and is useful where discharge time is not a factor, for example for smaller human doses in the order of 0.5 to 1.0 cc. However, for this case, the multiple exit port configuration has even greater utility for injecting more than one vaccine into the injection site at the same time. This is especially important for children where repeated use of needle injections is frightening, painful and very often difficult to complete because of adverse physical resistance, as well as the added expense of return visits to the health center or doctor's office. This type of patient reaction could lead to inadequate vaccinations and the possibility of unnecessary exposure to some very dangerous diseases. The multiple exit port solution makes use of a number N parallel, independent, barrel-type restraining chambers, one of which is shown as 845 in the cut-away view of barrel 840. Included in each of restraining chambers 845 is a different, inexpensive, thin-walled vaccine capsule and its exit port 842' that rests against a mating hole 838 in a forward access disk 844, shown as a broken out structure in FIG. 7GG. These capsules are similar to that described for FIG. 7E, but thinner in diameter to facilitate the side-by-side orientation. Each of the N capsules has its own piston 847 which interfaces with N geometrically matching rams 848 appended to a single central ram 849. Ram 849, and each of rams 848 moves to the left as shown in the drawing, pushing pistons 847 inward with the correct force when released from its position of stored mechanical energy. This configuration allows the health worker to rapidly dispense all injectants at the same time so that pain, fear, expense and resistance to injections are all dramatically reduced. In the description of FIGS. 7A and 7B, it was noted that a multiple chamber system similar to a revolver type pistol could be used for housing the vaccine capsules. The capsules can be loaded in the configuration of FIG. 7GG by sliding barrel 840 forward to expose the N mating carriages into which capsules 846 are inserted. The form-fitted outer portion of barrel 840 is then slid back into position to securely lock capsules 846 in place until the injection is completed. A trap door similar to door 708 described for FIG. 7E can also be used. Capsules 846 can be prefilled by the vaccine manufacturer and shipped to the health center, or they can be filled by the health worker with the appropriate vaccine when the person shows up for the injection. If jet or needle capsules of the type described for FIGS. 5A–5E are used, lyophilized serum can also be administered simultaneously with either the needle or jet orifice embodiment.

The multiple capsule system of FIG. 7GG and 7GG' has further utility by providing for different injection depth from each of the N injection chambers. This is accomplished by simply making a small change in the cross-sectional area of each of the capsules and its piston 847. Since central ram 849 will apply the same force to each of the independent rams 848, chamber pressure will depend on the cross-sectional area of the piston to which the force is applied. If this is done, slight changes in capsule does will occur since the distance of travel for all rams is the same because of their dependence on central ram 848. By the same token, the risk of error could be reduced because the containment chambers 845 can also have cross sections that wilt only accommodate a predetermined capsule. However, if consistent dose is an issue, further flexibility for injection depth is realized with slight modification to the diameter of the jet orifice for each capsule to facilitate a change of stream velocity for the known force, and injection depth will vary accordingly. Finally, different penetration depth for each capsule will help keep the injection products farther apart in the tissue, which in some cases is an important factor.

Figure 7H:
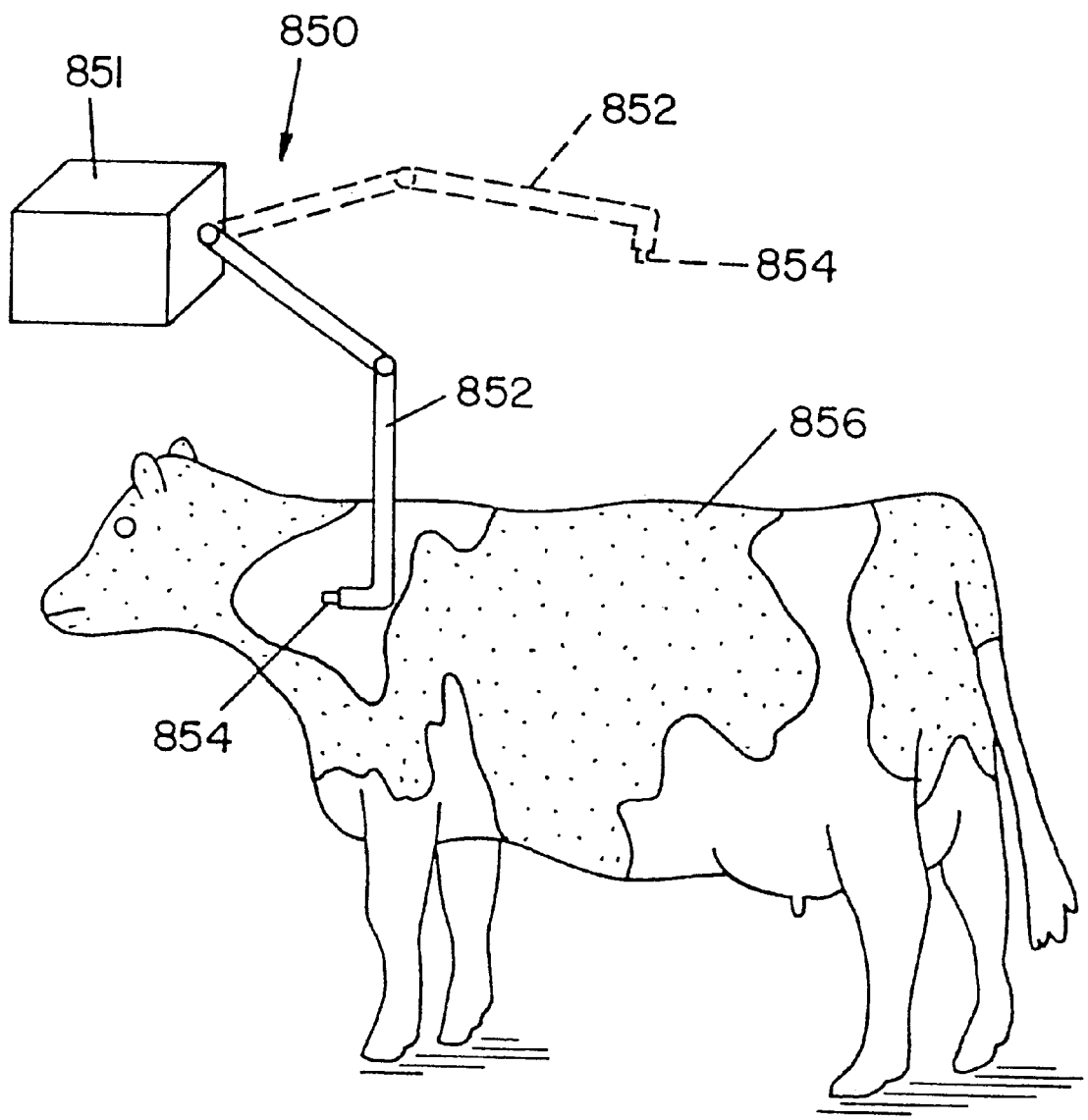
FIG. 7H is a pictorial view of a cow receiving a jet injection with a robotic arm according to another embodiment of the invention.

FIG. 7H illustrates a robotic system 850 for use with cattle 856 that are automatically identified and cut from the herd when an injection procedure is scheduled. The robotic system includes a control box 851 and an articulated, movable, mechanical arm 852 composed of injectant delivering tubes. This is a convenient time to mechanically restrain the animal, wherein arm 852 will move into position so a perforator 854 can contact the animal for a subsequent injection. The anchor point provided by the perforator is especially useful for a good injection because energetic movement by the animal is very likely at this time.

Further utility is provided if arm 852 of robotic system 850 is removable to provide a mobile, extended-arm injection system. A long, mobile injection system of this type will facilitate long range injections of large animals. This situation often arises if the animal is restrained at the neck, but requires an injection at a posterior portion of the body. The device is also useful when numerous animals are penned up, are in close proximity to each other, and are often lying down. For these situations, an extended arm on the order of one meter long will help simplify the injection procedure.

Figure 8A:
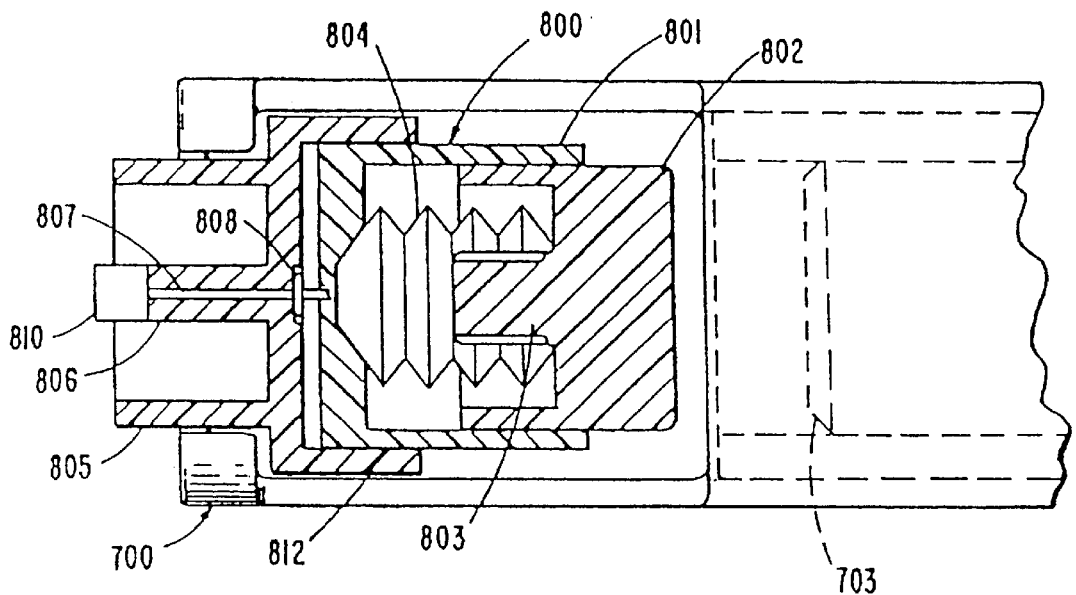
FIG. 8A shows a side, partial view of the jet injector system illustrated in FIG. 7 with a fresh cartridge installed therein.
Figure 8B:
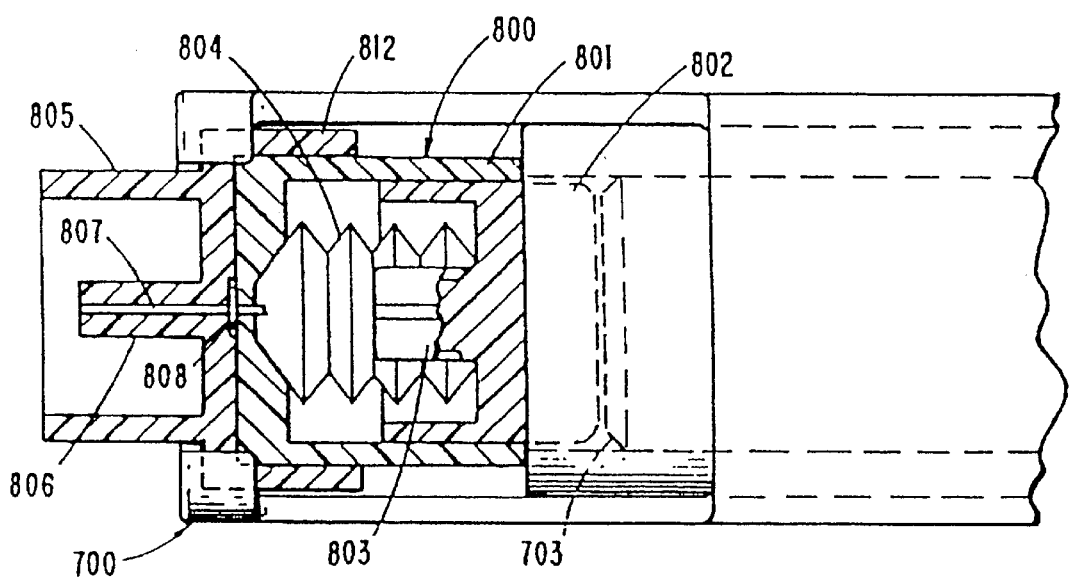
FIG. 8B shows a side, partial view of the jet injector system of FIG. 7 in which the cartridge has been breached.

The cartridge 800 is shown in detail in FIGS. 8A and 8B. Cartridge 800 comprises a sealed serum bellows 804 with a ram 803; a rear housing 801; a pressure piston 802; a front housing 812, which comprises a guard ring 805 and a jet output port 807 with a flange 808; and removable cap 810. FIG. 8A illustrates a fresh injector installed in the system of FIGS. 7, 7A or 7B prior to breaching the seal of serum bellows 804. As described elsewhere herein, cartridge 800 can be configured with a needle or perforator for delivery of the serum.

FIG. 8B illustrates the arrangements of FIG. 8A after the lever 702 of FIG. 7 is moved forward to breach the seal of the bellows 804 and to bring the injector piston 703 in position to drive the pressure piston 802 forward to collapse the bellows 804.

Figure 9B:
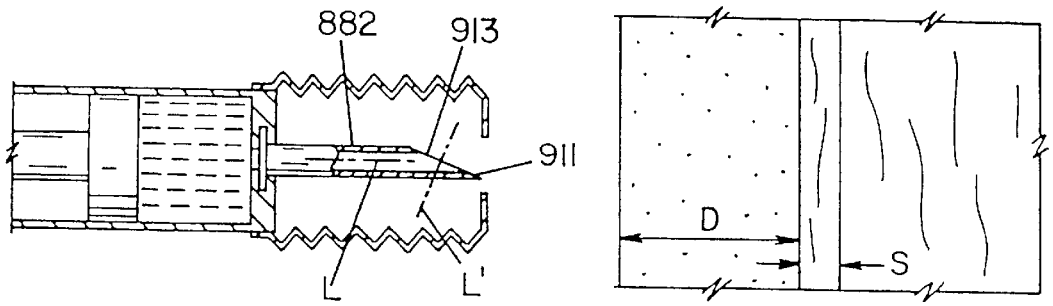
FIG. 9B is a schematic illustrating an encapsulated perforator prior to insertion, according to another embodiment of the invention.

FIGS. 9A–9D show the hide or dermis 860 of an animal such as a cow overlaying the subcutaneous space or layer 862, which in turn lays over a muscle 864. Dermis 860 has a thickness D and subcutaneous layer 862 has a thickness S. FIG. 9A illustrates the "pooling" effect that occurs when a capsule is used with a conventional needle and comprises an injection assembly 870 including a capsule 871, a cylindrical housing 872 and a plunger 874. A conventional hypodermic needle 876 is operatively connected to capsule 871, which holds an injectant 878. When plunger 874 is depressed, injectant 878 is ejected through the exit port of needle 876 and forms a pool 861 in muscle 864. Pooling often provokes an attack by the animal's immune system, thereby causing an encapsulation of the medication which often leads to abscesses and/or serious scarring of the tissue. In the case of feed animals, damage to the meat causes a significant economical loss to the industry, and in some cases, will provoke a level of infection that renders the animal useless.

FIG. 9B illustrates an injection assembly 880 having capsule 871 with housing 872 and plunger 874. A perforator 882 has a surgically sharp tip 883 at its delivery portion, and is attached to capsule 871 and enclosed with a collapsible protective housing 884. Perforator 882 has an attachment portion 914 for attachment to capsule 871. Collapsible housing 884 is in the form of a bellows having a free end 886 with walls 888 defining a circular opening 890 with a diameter larger than that of perforator 882. Housing 884 has an opposite end 892 which is fixed to the base of capsule 871.

Referring to FIG. 9BB, a detailed description of perforator 882 is shown. The perforator is of tubular construction, preferably made from stainless steel, having an effective length of no greater than the thickness of the dermis and subcutaneous layers of the skin or hide as discussed below. It has a slanted, surgically sharp tip 911 for being inserted into the skin or hide to provide a jet injection as explained hereinafter. Perforator 882 has a longitudinal, central axis L, and the slanted tip 911 has an oblong opening 913 with a central axis L' transverse to axis L. The slanted opening assists in preventing the delivery of foreign matter into a body during an injection with perforator 882. The slanted tip creates an anchor point to establish and maintain the penetration position of the delivery portion of the needle. It further maintains laminar flow of the jet stream emanating from the perforator, even if there is movement of the body being injected.

Figure 9C:
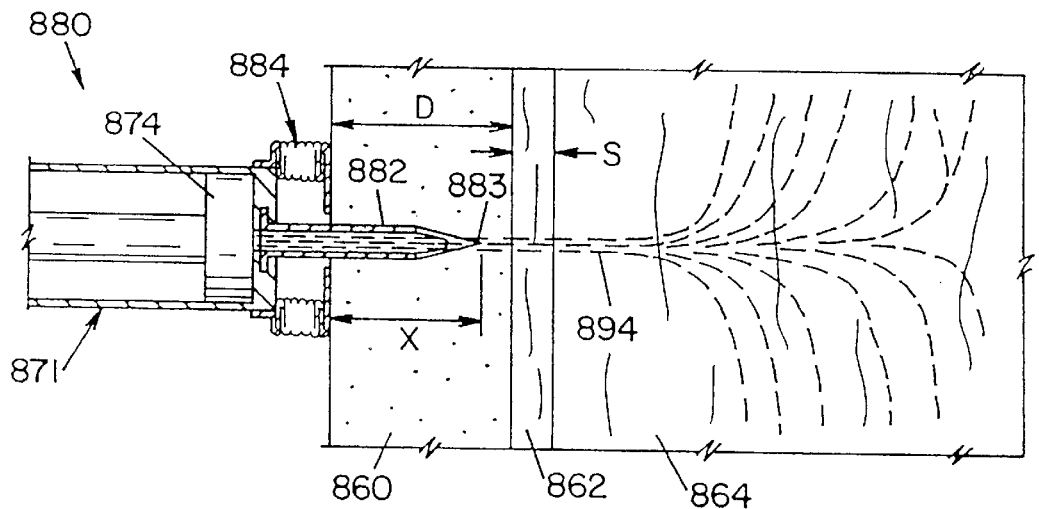
FIG. 9C shows in schematic the perforator of FIG. 9B inserted in the hide of an animal with a protective shield fully compressed.

In FIG. 9C, perforator 882 has been inserted into hide 860, but its tip 883 falls just short of the subcutaneous layer 862. Perforator 882 has an effective length X for insertion into the body having dermis 860, subcutaneous layer 862 and muscle 864 for an intramuscular or subcutaneous injection. Length X is less than the sum of thicknesses D and S of dermis 860 and subcutaneous layer 862 so that it does not enter muscle 864 during an injection. Plunger 874 has been depressed and housing 884 has been collapsed against hide 860, and tile injectant discharged to yield the penetrating jet stream 894 which will then deposit a vast majority of the injectant in the target area of the muscle 864, if that is the desired target, while leaving virtually none in the hide 860. If a subcutaneous injection is needed, one simply must reduce the injection pressure so that the jet stream will penetrate the remainder of the hide while not having enough energy to successfully penetrate the muscle.

Finally, while this entire discussion has focused on perforator advantages for an intramuscular injection, both veterinary and human immunologists have cited experimental evidence indicating that injections into the dermis may be many times more potent than that of the IM or subcutaneous regions, so much so, in fact, that greatly reduced volumes of the injectant may be possible. If continued research in this regard leads to a recommendation that certain injections be given in the dermis, the perforator concept is remarkably effective for this application as well, and actually provides additional advantages over that of the needle and syringe. To assure a perforator intradermal injection, one must simply shorten the length X so that it penetrates the outer layer while at the same time falling short of the subcutaneous space. In addition, if the pressure is reduced to the appropriate level, experimental work by the inventor on a freshly euthanized cow has shown that all of the injectant will remain in the dermis, with none at the surface, while also spreading the injectant over a much wider radius than that experienced with the pooling effect of the prior art needle and syringe. As with the IM or subcutaneous injection, the increased area and volume covered by the injectant will provide an increasingly rapid and effective pick-up by the immune system.

The range of thicknesses of the skin, hide or dermis for humans and a variety of animals is known, and are set forth below:

humans: 1.0 mm–12.7 mm cattle: 4 mm–8 mm goats: 1 mm–5 mm dogs: 1 mm (minimum thickness)

horses: 1 mm–5 mm pigs: 2.7 mm–4.7 mm

Therefore, for dermal injections, the perforator should be less than 1 mm for any animal (or person) such as humans, goats, dogs and horses at their minimum skin thickness, less than 2.7 mm for animals such as pigs, at their minimum skin thickness, and less than 4 mm for animals such as cattle at their minimum skin thickness. Likewise, the perforator could be longer for injecting into humans or other animals at thicker parts of their skin but less than 12.7 mm (humans), 5 mm (animals such as goats and horses), 4.7 mm (animals such as pigs) and 8 mm (animals such as cattle).

Figure 9D:
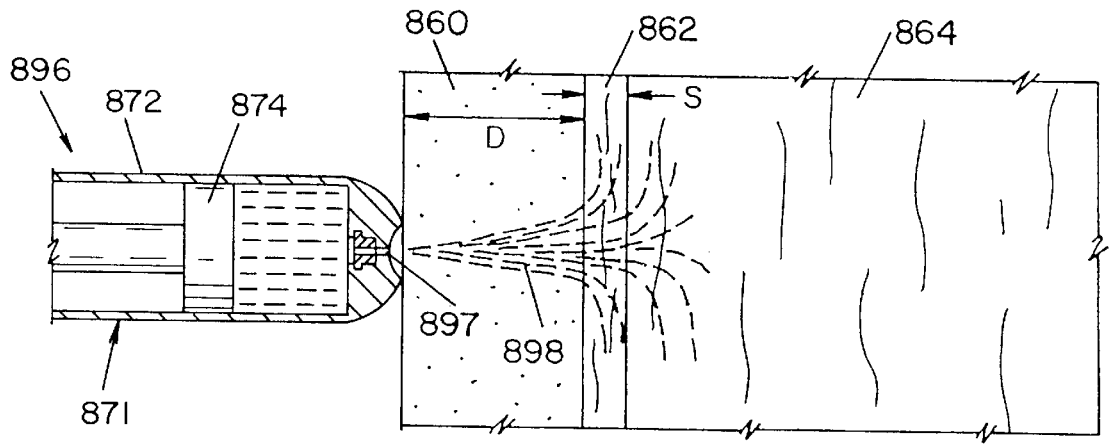
FIG. 9D shows in schematic form an injection system with jet stream degradation when the entrance point for the jet stream is the outer surface of the hide, under a prior art system.

FIG. 9D illustrates the jet stream coming from a conventional prior art flat injection orifice. An injection assembly 896 includes capsule 871 with housing 872 and plunger 874, and a flat jet orifice 897. When plunger 874 is depressed, a jet stream 898 is emitted, and beginning from the outer surface of the hide 860, the tough, hairy and often dirty conditions immediately often cause degradation of stream 898 so that a high percentage of the injectant remains on the outside, with very little, and in many cases, none of the injectant reaching subcutaneous space 862 or muscle 864, resulting in a much less effective injection, even if a dermal injection was intended.

Figure 9E:
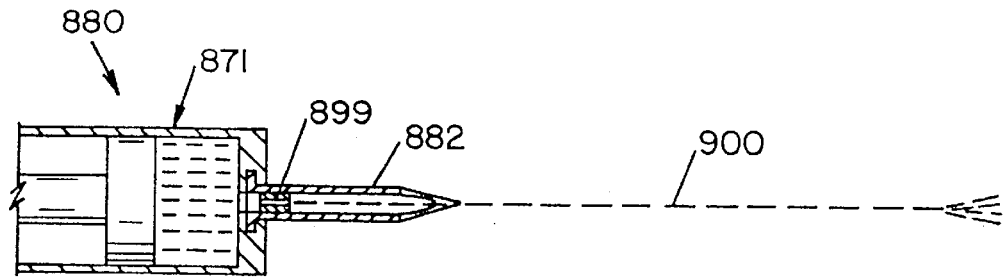
FIG. 9E is a schematic view of a perforator with a conventional jet orifice located at the input channel of the perforator.

FIG. 9E is an alternate embodiment of the invention showing perforator 882 from FIGS. 9B and 9C, but with a different orifice. In this case, a high quality, smaller diameter orifice 899 is located at the entrance end or port of perforator 882. When the jet injection is initiated, it will travel down the middle of perforator 882 without touching the walls and before encountering any of the animals hide or flesh. The very high quality, high coherency of such a flow pattern 900 will allow for much deeper muscle penetration with even less of the injectant being left behind in the dermis 860 or subcutaneous layer 862 if the objective is an intramuscular injection.

Figure 9F:
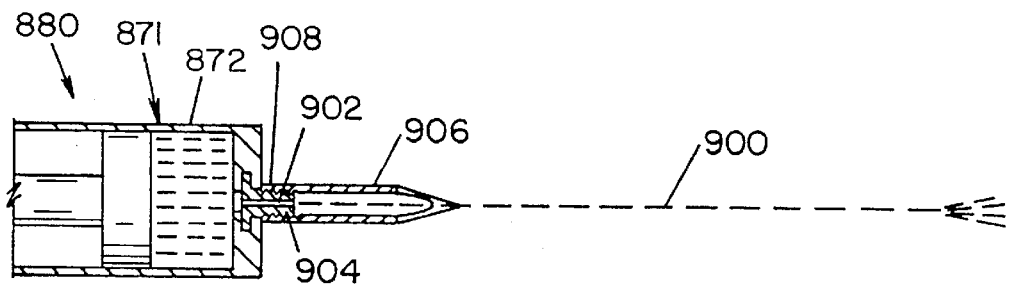
FIG. 9F is a schematic view of an embodiment of the invention showing a permanent jet orifice with a removable perforator.

FIG. 9F shows injection system 880 with a high quality orifice 902 connected to the injection chamber of housing 872, and having an externally threaded connector ring 904 affixed thereto. A perforator 906, similar to perforator 882 but having an internally threaded entrance end or port 908 for engagement with the threads on connector ring 904. The threaded connection between connector ring 904 and perforator 906 provides for an easy change of perforator 906 by simply unscrewing perforator 906. Other fast connect-disconnect devices can be used as well. The system emits jet stream 900 as noted with respect to FIG. 9E.

Figure 9G:
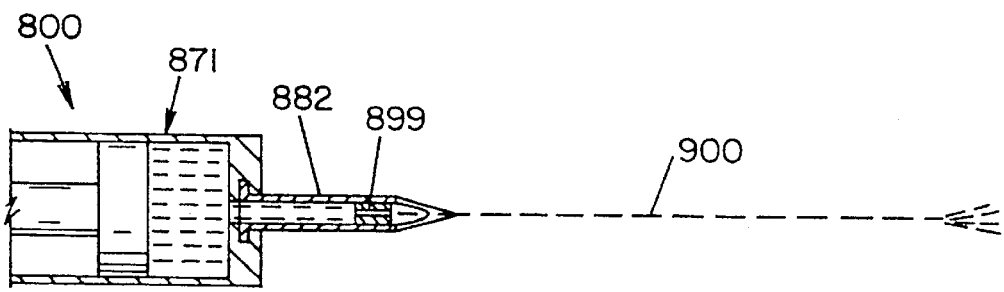
FIG. 9G shows schematically the jet orifice located at the exit end of the perforator pursuant to another embodiment of the invention.

System 800 in FIG. 9G is similar to that in FIG. 9E, except that the high quality orifice 899 is located at the exit end of perforator 882.

The injection systems according to the invention, such as shown for example in FIGS. 9B, 9E, 9F and 9G have generally flat front faces through which the perforator is extendable. The flat face helps prevent the hair and unsanitary material (such as that stuck on the hair) from being urged towards the injection site. The larger cross sectional area of contact around the injection site helps avoid the urging of tissue movement. The face need not be absolutely planar, but could have slight curves, a rough surface, indentations or the like, while preventing the urging of the foregoing movement.

Figure 9H:
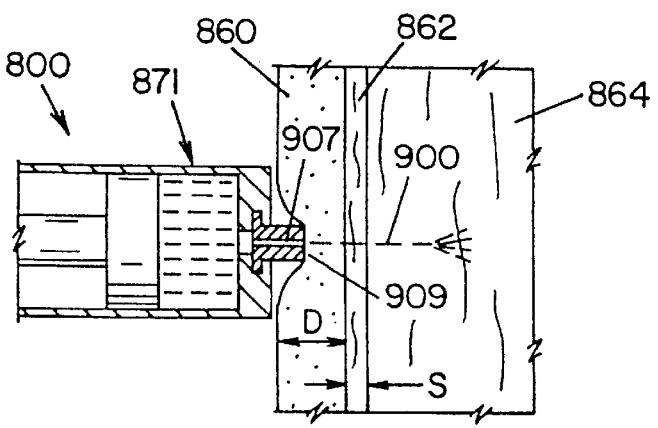
FIG. 9H shows a schematic view of a very short, flat, non-sharpened tubular orifice serving to stretch and detent the injection site in preparation for the high velocity jet stream according to a further embodiment of the invention.

Finally, FIG. 9H illustrates an adaptation derived from the perforator concept. In this embodiment, small diameter exit tube 907 extends about 2 to 4 mm from injector housing 871 and is configured with a non-sharpened, flat ended output. This diagram is not shown to scale and is drawn primarily for illustrative purposes. With this embodiment, there is no initial perforation, but it was found that the short protrusion will move aside any hair and both stretch and provide a detent at an injection site 909 when surface contact is made. Significant improvements in jet penetration is realized, while at the same time reducing the amount of injectant left at the surface as opposed to that of the prior art flat orifice of FIG. 9D. Benefits are found for human injections, for thinner hides of young calves and for other thin-skinned animal applications such as cats, dogs, fowl, etc.

The illustrative embodiments of our invention which are disclosed herein are but representative of our invention and many changes in form and function can be made without departing from the spirit and scope of our invention.

What is claimed is:

1. Apparatus for injecting fluid into a desired section of a body having an outer dermis and an inner region including at least a subcutaneous region and for some parts of the body, a muscular region, said apparatus comprising:

a fluid supplying device for supplying fluids at values of pressure and velocity of sufficient magnitude to generate a jet stream, and to inject a substantial amount of the fluid into a selected one of the outer dermis and the inner region; and a perforator for making a perforation and entering the dermis of the body, said perforator comprised of an elongated tubular member having a first end connected to said fluid supplying device and an opposed sharp second end for perforating the body and dispensing the jet stream of fluid into the perforation, said perforator having an effective length of less than 12.7 mm, said effective length preventing said perforator from perforating the muscular region;

said fluid supplying device having a generally flat face through which said perforator is extendable.

2. Apparatus according to claim 1 wherein said perforator has a longitudinal axis extending from said first end up to said second end, and said second end has a central axis slanted relative to the longitudinal axis of said perforator for enabling said second end to penetrate the dermis and create an anchor point to establish and maintain the penetration position of said second end, and maintain an effective fluid flow of the jet stream even if there is movement of the body being injected.

3. Apparatus according to 2 wherein said second end has a surgically sharp end for piercing the dermis.

4. Apparatus according to claim 1, and further comprising:

orifice means positioned in said perforator for generating a coherent stream for flow through said exit portion.

5. Apparatus according to claim 1, wherein said perforator has an effective length of less than 4 mm.

6. Apparatus according to claim 1, wherein said perforator has an effective length of less than 1.5 mm.

7. Apparatus according to claim 1, wherein said perforator has an effective length of less than 9.5 mm.

8. Apparatus according to claim 1, wherein said perforator has an effective length of less than 3.1 mm.

9. Apparatus according to claim 1, wherein said perforator has an effective length of less than 8 mm.

10. Apparatus according to claim 1, wherein said perforator has an effective length of less than 5 mm.

11. Apparatus according to claim 1, wherein said perforator has an effective length of less than 1 mm.

12. Apparatus according to claim 1, wherein said perforator has an effective length of less than 4.7 mm.

13. Apparatus according to claim 1, wherein said perforator has an effective length of less than 2.7 mm.

14. Apparatus according to claim 1, wherein said perforator has an effective length of less than 4.2 mm.

15. Apparatus according to claim 1, wherein said perforator has an effective length of less than 3.6 mm.

16. Apparatus according to claim 1 wherein said perforator is removable and replaceable with another perforator.

17. Apparatus according to claim 1 and further including protective containment means for protectively containing said perforator before and after said perforator makes a perforation and enters the dermis of the body.

18. Apparatus for injecting fluid into a desired section of a body having a dermis and an inner region including at least a subcutaneous region, and for some parts of the body a muscular region, said apparatus comprising:

an electro-mechanical, spring energized fluid supplying device for supplying fluids at values of pressure and velocity of sufficient magnitude to generate a jet stream, and to inject a substantial amount of the fluid into a selected one of the outer dermis and the inner region; and a perforator for making a perforation and entering the dermis of the body, said perforator comprised of an elongated tubular member having a first end connected to said fluid supplying device and an opposed sharp second end for perforating the body and dispensing the jet stream of fluid into the perforation, said perforator having an effective length of less than 12.7 mm, said effective length preventing said perforator from perforating the muscular region;

said fluid supplying device having a generally flat face through said perforator is extendable.

* * * * *